(12) United States Patent
Bazan et al.

(10) Patent No.: US 8,993,335 B2
(45) Date of Patent: Mar. 31, 2015

(54) METHODS FOR DETECTION AND ANALYSIS OF POLYNUCLEOTIDE-BINDING PROTEIN INTERACTIONS

(75) Inventors: Guillermo C. Bazan, Santa Barbara, CA (US); Shu Wang, Goleta, CA (US); Bin Liu, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 979 days.

(21) Appl. No.: 10/779,412

(22) Filed: Feb. 13, 2004

(65) Prior Publication Data

US 2005/0003386 A1    Jan. 6, 2005

Related U.S. Application Data

(60) Provisional application No. 60/447,860, filed on Feb. 13, 2003.

(51) Int. Cl.
| | | |
|---|---|---|
| *G01N 33/00* | (2006.01) | |
| *C12Q 1/68* | (2006.01) | |
| *C07K 1/00* | (2006.01) | |
| *C07H 21/02* | (2006.01) | |

(52) U.S. Cl.
CPC .................................. *C12Q 1/6818* (2013.01)
USPC .............. 436/94; 435/6.1; 530/350; 536/23.1

(58) Field of Classification Search
USPC ..................... 435/5, 6; 436/94, 800; 536/23.1; 530/350
See application file for complete search history.

(56) References Cited

U.S. PATENT DOCUMENTS

| | | | |
|---|---|---|---|
| 4,948,843 A | 8/1990 | Roberts et al. | |
| 4,950,587 A | 8/1990 | Roberts et al. | |
| 5,408,109 A | 4/1995 | Heeger et al. | |
| 5,612,221 A | 3/1997 | Simons et al. | |
| 5,869,350 A | 2/1999 | Heeger et al. | |
| 5,881,083 A | 3/1999 | Diaz-Garcia et al. | |
| 5,965,108 A * | 10/1999 | Dean ........................... | 424/1.69 |
| 5,968,762 A | 10/1999 | Jadamec et al. | |
| 5,990,479 A | 11/1999 | Weiss et al. | |
| 5,998,135 A | 12/1999 | Rabbani et al. | |
| 6,090,552 A | 7/2000 | Nazarenko et al. | |
| 6,263,286 B1 | 7/2001 | Gilmanshin et al. | |
| 6,268,222 B1 * | 7/2001 | Chandler et al. .............. | 436/523 |
| 6,280,933 B1 | 8/2001 | Glazer et al. | |
| 6,350,431 B1 | 2/2002 | Snow et al. | |
| 6,534,329 B2 | 3/2003 | Heeger et al. | |
| 6,545,164 B1 | 4/2003 | Waggoner et al. | |
| 6,579,726 B1 | 6/2003 | Natan et al. | |
| 6,589,731 B1 | 7/2003 | Chen et al. | |
| 6,743,640 B2 | 6/2004 | Whitten | |
| 6,808,542 B2 | 10/2004 | Nguyen et al. | |
| 6,951,682 B1 | 10/2005 | Zebala | |
| 6,979,543 B2 | 12/2005 | Chen et al. | |
| 7,122,383 B2 | 10/2006 | Jones et al. | |
| 7,141,437 B2 | 11/2006 | Dvornic et al. | |
| 7,208,122 B2 | 4/2007 | Swager et al. | |
| 7,214,489 B2 | 5/2007 | Bazan et al. | |
| 7,270,956 B2 | 9/2007 | Bazan et al. | |
| 7,767,405 B2 * | 8/2010 | Gillies et al. .................... | 435/7.1 |
| 2001/0026921 A1 | 10/2001 | Rabbani et al. | |
| 2002/0009728 A1 | 1/2002 | Bittner | |
| 2002/0034747 A1 | 3/2002 | Bruchez | |
| 2002/0150759 A1 | 10/2002 | Jones | |
| 2002/0177136 A1 | 11/2002 | McBranch | |
| 2003/0054413 A1 | 3/2003 | Kumaraswamy | |
| 2003/0087311 A1 | 5/2003 | Wolf | |
| 2004/0009506 A1 | 1/2004 | Stephan et al. | |
| 2004/0023248 A1 | 2/2004 | O'Malley | |
| 2004/0023317 A1 | 2/2004 | Motamedi et al. | |
| 2004/0121337 A1 | 6/2004 | Deans et al. | |
| 2004/0241768 A1 | 12/2004 | Whitten | |
| 2005/0003386 A1 | 1/2005 | Bazan et al. | |
| 2005/0064239 A1 | 3/2005 | Takei | |
| 2005/0064604 A1 | 3/2005 | Bohmann et al. | |
| 2005/0196775 A1 | 9/2005 | Swager et al. | |
| 2006/0073607 A1 | 4/2006 | Rose et al. | |
| 2006/0127929 A1 | 6/2006 | Swager | |
| 2006/0183140 A1 | 8/2006 | Bazan et al. | |
| 2006/0216734 A1 | 9/2006 | Bazan et al. | |
| 2006/0216759 A1 | 9/2006 | Naasani | |

(Continued)

FOREIGN PATENT DOCUMENTS

| | | |
|---|---|---|
| EP | 0708837 | 1/1995 |
| EP | 0684239 | 5/1995 |

(Continued)

OTHER PUBLICATIONS

"Viruses" (Wikipedia.com, accessed Nov. 24, 2012).*
"How many species of bacteria are there" (wisegeek.com; accessed Sep. 23, 2011).*
"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*

(Continued)

*Primary Examiner* — Bradley L Sisson
(74) *Attorney, Agent, or Firm* — Bret E. Field; Bozicevic, Field & Francis LLP

(57) ABSTRACT

Methods, compositions and articles of manufacture for assaying a sample for a target polynucleotide are provided. A sample suspected of containing the target polynucleotide is contacted with a polycationic multichromophore and a sensor PBP that can bind to the target polynucleotide. The sensor PBP comprises a signaling chromophore to absorb energy from the excited multichromophore and emit light in the presence of the target polynucleotide. The methods can be used in multiplex form. Kits comprising reagents for performing such methods are also provided.

17 Claims, 9 Drawing Sheets

(8 of 9 Drawing Sheet(s) Filed in Color)

(56) References Cited

U.S. PATENT DOCUMENTS

| | | | |
|---|---|---|---|
| 2007/0178470 | A1 | 8/2007 | Bissonnette et al. |
| 2008/0038751 | A1 | 2/2008 | Asberg et al. |

FOREIGN PATENT DOCUMENTS

| | | |
|---|---|---|
| EP | 0990903 | 4/2000 |
| EP | 1279023 | 9/2001 |
| EP | 1281744 | 5/2003 |
| WO | WO 99/35288 A1 | 7/1999 |
| WO | WO 00/14278 A1 | 3/2000 |
| WO | WO 00/66790 A1 | 11/2000 |
| WO | WO 01/01144 | 1/2001 |
| WO | WO 01/95059 | 12/2001 |
| WO | WO 02/081735 A2 | 10/2002 |
| WO | WO 02/084271 | 10/2002 |
| WO | WO 03/102239 | 12/2003 |
| WO | WO 2004/001379 A2 | 12/2003 |
| WO | WO 2004/037886 | 5/2004 |
| WO | WO 2004/077014 | 9/2004 |
| WO | WO 2005/056628 | 6/2005 |
| WO | WO 2006/092063 | 9/2006 |
| WO | WO 2007/001438 | 1/2007 |

OTHER PUBLICATIONS

Balakin, K.V. et al. Conjugates of oligonucleotides with polyaromatic fluorophores as promising DNA probes[1;] *Biosensors and Bioelectronics* (1998) 13:771-778.

Bardea, A. et al. Sensing and amplification of oligonucleotide-DNA interactions by means of impedance spectroscopy: a route to a Tay-Sachs sensor; *Chem. Commun.* (1999) 21-22.

Baur, J.W., et al. Thin-Film Light-Emitting Devices Based on Sequentially Adsorbed Multilayers of Water-Soluble Poly (p-phenylene)s; *Advanced Materials* (1998) 10:17:1452-1455.

Behr, J.P. Synthetic Gene-Transfer Vectors; *Acc. Chem. Res.* (1993) 26: 274-278.

Behr, J.P. DNA Strongly Binds to Micelles and Vesicles Containing Lipopolyamines or Lipointercalants; *Tetrahedron Lett.* (1986) 27:48:5861-5864.

Benson, S.C. et al. Heterodimeric DNA-binding dyes designed for energy transfer: synthesis and spectroscopic properties; *Nucleic Acids Res.* (1993) 21:24:5727-5735.

Betts, L., et al. A Nucleic Acid Triple Helix Formed by a Peptide Nucleic Acid-DNA Complex; *Science* (1995) 270: 1838-1841.

Bhattacharya, S. and Mandal, S.S. Interaction of surfactants with DNA. Role of hydrophobicity and surface charge on intercalation and DNA melting; *Biochim.et Biophys. Acta.* (1997) 1323:29-44.

Bhattacharya, S. and Mandal, S.S. Role of hydrophobic effect and surface charge in surfactant-DNA association; *Indian J. Biochem. & Biophys.* (1997) 34:11-17.

Bier, F.F. and Kleinjung, F. Feature-size limitations of microarray technology—a critical review; *Fresenius J. Anal. Chem.* (2001) 371:151-156.

Birnboim, H.C. and Jevcak, J.J. Fluorometric Method for Rapid Detection of DNA Strand Breaks in Human White Blood Cells Produced by Low Doses of Radiation; *Cancer Res.* (1981) 41:1889-1892.

Blessing, T. et al. Monomolecular collapse of plasmid DNA into stable virus-like particles; *Proc. Natl. Acad. Sci. USA* (1998) 95:1427-1431.

Bronich, T.K. et al. Recognition of DNA Topology in Reactions between Plasmid DNA and Cationic Copolymers; *J. Am. Chem. Soc.* (2000) 122:35:8339-8343.

Cardullo, R.A. et al. Detection of nucleic acid hybridization by nonradiative fluorescence resonance energy transfer; *Proc. Natl. Acad. Sci. USA* (1988) 85:8790-8794.

Castro, A. and Williams, J.G.K. Single-molecule detection of specific nucleic acid sequences in unamplified genomic DNA; *Anal. Chem.* (1997) 69:19:3915-3920.

Chandar, P. et al. Fluorescence probe investigation of anionic polymer-cationic surfactant interactions; *Macromolecules* (1988) 21:950-953.

Chehab, F.F. and Kan, Y.W. Detection of specific DNA sequences by fluorescence amplification: A color complementation assay; *Proc. Nat. Acad. Sci. USA* (1989) 86:9178-9182.

Chen, L. and Frankel, A.D. A peptide interaction in the major groove of RNA resembles protein interactions in the minor groove of DNA; *Proc. Natl. Acad. Sci. USA*. (1995) 92:5077-5081.

Chen, L. et al. Highly sensitive biological and chemical sensors based on reversible fluorescence quenching in a conjugated polymer, *Proc. Natl. Acad. Sci. USA*. (1999) 96:22:12287-12292.

Chen, W. et al. Using Ethidium Bromide to Probe the Interactions between DNA and Dendrimers; *Langmuir* (2000) 16:15-19.

Delling, U. et al. The number of positively charged amino acids in the basic domain of Tat is critical for trans-activation and complex formation with TAR RNA; *Proc. Natl. Acad. Sci. USA* (1991) 88:6234-6238.

Demidov, V.V. PNA and LNA throw light on DNA; *Trends in Biotechnology* (2003) 21:1:4-7.

Demidov, V.V. et al. Stability of peptide nucleic acids in human serum and cellular extracts; *Biochem. Pharmacol.* (1994) 48:6:1310-1313.

Didenko, V.V. DNA Probes Using Fluorescence Resonance Energy Transfer (FRET): Designs and Applications; *BioTechniques* (2001) 31:5:1106-1121.

Dogariu, A. et al. Time-resolved Förster energy transfer in polymer blends; *Synthetic Metals* (1999) 100:95-100.

Dufourcq, J. et al. Molecular assembling of DNA with amphipathic peptides; *FEBS Lett.* (1998) 421:7-11.

Eastman, S.J. et al. Biophysical characterization of cationic lipid: DNA complexes; *Biochim. et Biophys. Acta* (1997) 1325:41-62.

Egholm, M. et al. PNA hybridizes to complementary oligonucleotides obeying the Watson-Crick hydrogenbonding rules; *Nature* (1993) 365:566-568.

Egholm, M. et al. Recognition of Guanine and Adenine in DNA by Cytosine and Thymine Containing Peptide Nucleic Acids (PNA); *J. Am. Chem. Soc.* (1992) 114:9677-9678.

Englebienne, P. Synthetic materials capable of reporting biomolecular recognition events by chromic transition; *J. Mater Chem.* (1999) 9:1043-1054.

Eskilsson, K. et al. DNA-Surfactant Complexes at Solid Surfaces; *Langmuir* (2001) 17:1666-1669.

Felgner, P.L. et al. Nomenclature for Synthetic Gene Delivery Systems; *Hum. Gene Ther.* (1997) 8:511-512.

Ferguson, B.Q. and Yang, D.C.H. Localization of Noncovalently Bound Ethidium in Free and Methionyl-tRNA Synthetase Bound tRNA$^{fMet}$ by Singlet-Singlet Energy Transfer; *Biochemistry* (1986) 25:5298-5304.

Fernandez-Saiz, M. et al. A Cationic Cydophane That Forms a Base-Pair Open Complex with RNA Duplexes; *J. Am. Chem. Soc.* (1996) 118:4739-4745.

Frankel, A.D. Peptide models of the Tat-TAR protein-RNA interaction; *Prot Sci.* (1992) 1:1539-1542.

Futami, J. et al. Optimum Modification for the Highest Cytotoxicity of Cationized Ribonuclease; *J. Biochem.* (2002) 132:223-228.

Gallego, J. and Varani, G. Targeting RNA with Small-Molecule Drugs: Therapeutic Promise and Chemical Challenges; *Acc. Chem. Res.* (2001) 34:10:836-843.

Gallo, R and Montagnier, L. AIDS in 1988; *Sci. Am.* (1988) 259:4: 41-48.

Ganachaud, F. et al. Adsorption of Single-Stranded DNA Fragments onto Cationic Aminated Latex Particles; *Langmuir* (1997) 13:701-707.

Gaylord, B. S. et al. DNA detection using water-soluble conjugated polymers and peptide nucleic acid probes; *Proc. Natl. Acad. Sci. USA* (2002) 99:17:10954-10957.

Gaylord, B.S. et al. Water-Soluble Conjugated Oligomers: Effect of Chain Length and Aggregation on Photoluminescence-Quenching Efficiencies; *J. Am. Chem. Soc.* (2001) 123:6417-6418.

Gaylord, B.S. et al. DNA Hybridization Detection with Water-Soluble Conjugated Polymers and Chromophore-Labeled Single-Stranded DNA; *J. Am. Chem. Soc.* (2003) 125:896-900.

(56) References Cited

OTHER PUBLICATIONS

Gershon, H. et al. Mode of Formation and Structural Features of DNA-Cationic Liposome Complexes Used for Transfection; *Biochemistry* (1993) 32:7143-7151.

Giesen, U. et al. A formula for thermal stability ($T_m$) prediction of PNA/DNA duplexes; *Nucleic Acids Res.* (1998) 26:21:5004-5006.

Gössl, L. et al. Molecular Structure of Single DNA Complexes with Positively Charged Dendronized Polymers; *J. Am. Chem. Soc.* (2002) 124:6860-6865.

Hage, D.S.. Immunoassays; *Anal. Chem.* (1999) 71:12:294R-304R.

Hanvey, J.C. et al. Antisense and Antigene Properties of Peptide Nucleic Acids; *Science* (1992) 258:1481-1485.

Harada, A. and Kataoka, K. Chain Length Recognition: Core-Shall Supramalecular Assembly from Oppositely Charged Block Copolymers; *Science* (1999) 283:65-67.

Ho, H.A. et al. Colorimetric and Fluorometric Detection of Nucleic Acids Using Cationic Polythiophene Deriatives; *Angew. Chem. Int. Ed.* (2002) 41:9:1548-1551.

Izumrudov, V.A. et al. The influence of chain length of a competitive polyanion and nature of monovalent counterions on the direction of the substitution reaction of polyelectrolyte complexes; *Makromol. Chem., Rapid Commun.* (1988) 9:7-12.

Izumrudov, V.A. et al. Competitive Reactions in Solutions of DNA and Water-Soluble Interpolyelectrolyte Complexes; *Biopolymers* (1995) 35:523-531.

Izumrudov, V.A. et al. Competitive Displacement of Ethidium Cations Intercalated in DNA by Polycations; *Dokl. Phys. Chem.* (1995) 342:Nos. 4-6: 150-153.

Izumrudov, V.A. et al. Ethidium Bromide as a Promising Probe for Studying DNA Interaction with Cationic Amphiphiles and Stability of the Resulting Complexes; *Langmuir* (2002) 18:10348-10356.

Izumrudov, V.A. et al. Controllable Stability of DNA-Containing Polyelectrolyte Complexes in Water-Salt Solutions; *Biopolymers.* (1999) 52:94-108.

Izumrudov, V.A. and Zhiryakova, M.V. Stability of DNA-containing interpolyelectrolyte complexes in water-salt solutions; *Macromol. Chem. Phys.* (1999) 200:11:2533-2540.

Jain, C. and Belasco, J.G. Rapid Genetic Analysis of RNA-Protein Interactions by Translational Repression in *Escherichia coli; Methods Enzymol.* (2000) 318:309-332.

Jenkins, Y. and Barton, J.K. A Sequence-Specific Molecular Light Switch: Tethering of an Oligonucleotide to a Dipyridophenazine Complex of Ruthenium (II); *J. Am. Chem. Soc.* (1992) 114:8736-8738.

Johansson, M.K. et al. Intramolecular Dimers: A New Strategy to Fluorescence Quenching in Dual-Labeled Oligonucleotide Probes; *J. Am. Chem. Soc.* (2002) 124:6950-6956.

Kabanov, A.V. et al. DNA Interpolyelectrolyte Complexes as a Tool for Efficient Cell Transformation; *Biopolymers.* (1991) 31:1437-1443.

Kabanov, A.V. and Kabanov, V.A. DNA Complexes with Polycations for the Delivery of Genetic Material into Cells; *Bioconjugate Chem.* (1995) 6:7-20.

Kabanov, V.A. et al. Cooperative Interpolyelectrolyte Reactions; *Makromol. Chem. Suppl.* (1985) 13:137-155.

Karn, J. et al. HIV A Practical Approach; RNA binding assays for the regulatory proteins Tat and Rev; *IRL Press, New York*; (1995) 9:147-165.

Katayose, S. and Kataoka, K. Water-Soluble Polyion Complex Associates of DNA and Poly(ethylene glycol)-Poly($_L$-lysine) Block Copolymer; *Bioconjugate Chem.* (1997) 8:702-707.

Kircheis, R. et al. Tumor targeting with surface-shielded ligand-polycation DNA complexes; *J. Controlled Release*; (2001) 72:165-170.

Kirsh, Yu. E. et al. Comparison of Properties of an Oxime-Bound Partially Quaternized Poly-4-Vinylpyridine and a Monomer Analogous Oxime; *Eur. Polym. J.* (1974) 10:393-399.

Knemeyer, J. et al. Probes for Detection of Specific DNA . . . *Anal. Chem.* (2000) 72:3717-3724.

Kwon, I.C. et al. Electrically Erodible polymer gel for controlled release of drugs; *Nature* (1991) 354:291-293.

Leclerc M. Optical and Electrochemical Transducers Based on Functionalized Conjugated Polymers; *Adv. Mater*, (1999) 11:18:1491-1498.

Lee, M.A. et al. ResonSense®: simple linear fluorescent probes for quantitative homogeneous rapid polymerase chain reaction; *Anal. Chim. Acta* (2002) 457:61-70.

Le-Pecq, J.B. and Paoletti, C. A Fluorescent Complex between Ethidium Bromide and Nucleic Acids; *J. Mol Biol.* (1967) 27:87-106.

Leulliot, N. and Varani, G. Current Topics in RNA-Protein Recognition: Control of Specificity and Biological Function through Induced Fit and Conformational Capture; *Biochemistry* (2001) 40:27:7947-7956.

Liu, B. et al. Effect of Chromophore-Charge Distance on the Energy Transfer Properties of Water-Soluble Conjugated Oligomers; *J. Am. Chem. Soc.* (2003) 125:6705-6714.

Makino, S. et al. Molecular Characterization and Protein Analysis of the *cap* Region, Which is Essential for Encapsulation in *Bacillus anthracis; J. Bacteriol.* (1989) 171:2:722-730.

Manning, G.S. Thermodynamic Stability Theory for DNA Doughnut Shapes Induced by Charge Neutralization; *Biopolymers.* (1980) 19:37-59.

Manning, G.S. The Possibility of Intrinsic Local Curvature in DNA Toroids; *Biopolymers.* (1981) 20:1261-1270.

Manning, G.S. The molecular theory of polyelectrolyte solutions with applications to the electrostatic properties of polynucleotides; *Qrtly Review of Biophysics.* (1978) v.11: 179-246.

Maruyama, A. et al. Characterization of Interpolyelectrolyte Complexes between Double-Stranded DNA and Polylysine Comb-Type Copolymers Having Hydrophilic Side Chains; *Bioconjugate Chem.* (1998) 9:292-299.

Matsumoto, C; et al. High-Throughput Screening Utilizing Intramolecular Fluorescence Resonance Energy Transfer for the Discovery of the Molecules that Bind HIV-1 TAR RNA Specifically; *Bioorg. Med. Chem. Lett.* (2000) 10:1857-1861.

McLoughlin, D.M. et al. A simple and effective separation and purification procedure for DNA fragments using Dodecyltrimethylammonium bromide; *Bioseparation.* (2001) 9:307-313.

McQuade, D.T. et al. Conjugated Polymer-Based Chemical Sensors; *Chem. Rev.* (2000) 100:2537-2574.

McQuade, D.T. et al. Signal amplification of a "Turn-On" Sensor: Harvesting the Light Captured by a Conjugated Polymer; *J. Am. Chem. Soc.* (2000) 122:12389-12390.

Mel'Nikov, S.M. et al. Discrete Coil—Globule Transition of Large DNA Induced by Cationic Surfactant; *J. Am. Chem. Soc.* (1995) 117:2401-2408.

Mergny, J.L. et al. Fluorescence Energy Transfer between Two Triple Helix-Forming Oligonucleotides Bound to Duplex DNA; *Biochemistry.* (1994) 33:15321-15328.

Miao, Y.J. et al. Photophysics of Poly(paracyclophan-1-ene) and Derivatives: Evidence for Intrachain Energy Transfer and Chromophore Aggregation; *J. Am. Chem. Soc.* (1995) 117:11407-11420.

Miller, I.R. and Bach, D. Interaction of DNA with Heavy Metal Ions and Polybases: Cooperative Phenomena; *Biopolymers.* (1968) 6:169-179.

Minehan, D.S. et al. Kinetics of DNA Binding to Electrically Conducting Polypyrrole Films; *Macromolecules.* (1994) 27:777-783.

Morgan, A.R. and Pulleyblank, D.E. Native and Denatured DNA, Cross-Linked and Palindromic DNA and Circular Covalently-Closed DNA Analysed by a Sensitive Fluorometric Procedure; *Biochem. Biophys. Res. Commun.* (1974) 61:2:396-403.

Nielsen, P.E. Applications of peptide nucleic acids, *Analytical biotechnology.* (1999) 10:71-75.

Nguyen, H-K, et al. Nonviral Transfer Technology: Evaluation of polyether-polyethyleneimine graft copolymers as gene transfer agents; *Gene Ther.* (2000) 7:126-138.

Nishanian, P. et al. A Simple Method for Improved Assay Demonstrates that HIV p24 Antigen is Present as Immune Complexes in Most Sera from HIV-Infected Individuals; *J. Infect. Dis.* (1990) 162:21-28.

(56) References Cited

OTHER PUBLICATIONS

Nuovo, G.J. In Situ Localization of PCR-Amplified DNA and cDNA; *Methods Mol. Bio.* (2000) 123:217-238.

Olins, D.E. et al. Model Nucleoprotein Complexes: Studies on the Interaction of Cationic Homopolypeptides with DNA; *J. Mol. Biol.* (1967) 24:157-176.

Pasternack, R.F. et al. Long-Range Fluorescence Quenching of Ethidium Ion by Cationic Porphyrins in the Presence of DNA; *J. Am. Chem. Soc.* (1991) 113:6835-6840.

Patolsky, F. et al. Amplified DNA Detection by Electrogenerated Biochemiluminescence and by the Catalyzed Precipitation of an Insoluble Product on Electrodes in the Presence of the Doxorubicin Intercalator; *Angew. Chem. Int. Ed.* (2002) 41:18:3398-3402.

Patolsky, F. et al. Electronic Transduction of DNA Sensing Processes on Surfaces: Amplification of DNA Detection and Analysis of Single-Base Mismatches by Tagged Liposomes; *J. Am Chem. Soc.* (2001) 123:5194-5205.

Peterlinz, K.P. et al. Observation of Hybridization and Dehybridization of Thiol-Tethered DNA using Two-Color Surface Plasmon Resonance Spectroscopy; *J. Am. Chem. Soc.* (1997) 119:3401-3402.

Petty, J.T. et al. Thermodynamic Characterization of the Association of Cyanine Dyes with DNA; *J. Phys. Chem. B.* (2000) 104:7221-7227.

Pilipenko, E.V. et al. A cell cycle-dependent protein serves as a template-specific translation initiation factor; *Genes & Dev.* (2000) 14:2028-2045.

Pinto, M.R. and Schanze, K.S. Conjugated Polyelectrolytes: Synthesis and Applications; *Synthesis.* (2002) 9:1293-1309.

Plank, C. et al. Branched Cationic Peptides for Gene Delivery: Role of Type and Number of Cationic Residues in Formation and in Vitro Activity of DNA Polyplexes; *Hum. Gene Ther.* (1999) 10:319-332.

Portela, A. and Digard, P. The influenza virus nucleoprotein: a multifunctional RNA-binding protein pivotal to virus replication; *J. Gen. Virol.* (2002) 83:723-734.

Puglisi, J.D. et al. Conformation of the TAR RNA-Arginine Complex by NMR Spectroscopy; *Science.* (1992) 257:76-80.

Pullman, B. et al. Two Aspects of DNA Polymorphism and Microheterogeneity: Molecular Electrostatic Potential and Steric Accesibility; *J. Biochem.* (1982) 124:229-238.

Richter, S. et al. Specific HIV-1 TAR RNA Loop Sequence and Functional Groups are Required for Human Cydin T1-Tat-TAR Ternary Complex Formation; *Biochemistry.* (2002) 41:6391-6397.

Saghatelian, A. et al. DNA Detection and Signal Amplification via an Engineered Allosteric Enzyme; *J. Am. Chem. Soc.* (2003) 125:344-345.

Saiki, R.K. et al. Enzymatic Amplification of β-Globin Genomic Sequences and Restriction Site Analysis for Diagnosis of Sickle Cell Enemia; *Science.* (1985) 230:1350-1354.

Schork, N.J. et al. Single nucleotide polymorphisms and the future of genetic epidemiology; *Clin. Genet.* (2000) 58:250-264.

Seymour, L.W. et al. Cationic block copolymers as self-assembling vectors for gene delivery; *Self-assembling Complexes for Gene Delivery*; (1998) 11:219-239.

Shinozuka, K. et al. A Novel Multifunctionality Labelled DNA Probe Bearing an Intercalator and a Fluorophore; *J. Chem. Soc., Chem. Commun.* (1994) 1377-1378.

De Smedt, S.C. et al. Cationic Polymer Based Gene Delivery Systems; *Pharm. Res.* (2000) 17:2:113-126.

Smith, J.O. et al. Molecular Recognition of PNA-Containing Hybrids: Spontaneous Assembly of Helical Cyanine Dye Aggregates on PNA Templates; *J. Am. Chem. Soc.* (1999) 121:2686-2695.

Smith, P. et al. Surfactant structure around DNA in aqueous solution; *Phys. Chem. Chem. Phys.* (2000) 2:1305-1310.

Stender, H. et al. PNA for rapid microbiology; *J. Microbiological Methods.* (2002) 48:1-17.

Stork, M. et al. Energy Transfer in Mixtures of Water-Soluble Oligomers: Effect of Charge, Aggregation, and Surfactant Complexatlon; *Adv. Mater.* (2002) 14:5:361-366.

Su, X et al. Au nanoparticle- and silver-enhancement reaction-amplified microgravimetric biosensor; *Chem. Commun.* (2001) 755-756.

Sullenger, B.A. and Gilboa, E. Emerging clinical applications of RNA; *Nature.* (2002) 418:252-258.

Takakusa, H. et al. Design and Synthesis of an Enzyme-Cleavable Sensor Molecule for Phosphodiesterase Activity Based on Fluorescence Resonance Energy Transfer; *J. Am. Chem. Soc.* (2002) 124:8:1653-1657.

Tamilarasu, N. et al. A New strategy for Site-Specific Protein Modification: Analysis of a Tat Peptide-TAR RNA Interaction; *Bioconjugate Chem.* (2001) 12:2:135-138.

Tang, M.X. and Szoka, F.C. The influence of polymer structure on the interactions of cationic polymers with DNA and morphology of the resulting complexes; *Gene Ther.* (1997) 4:823-832.

Demers, L.M. et al. Thermal Desorption: *J. Am. Chem. Soc.* (2002) 124, 11248-11249.

Taton, T.A. et al. Scanometric DNA Array Detection with Nanoparticle Probes; *Science.* (2000) 289:1757-1760.

Taton, T.A. et al. Two-Color Labeling of Oligonucleotide Arrays via Size-Selective Scattering of Nanoparticle Probes; *J. Am. Chem. Soc.* (2001) 123:5164-5165.

Tomac, S. et al. Ionic Effects on the Stability and Conformation of Peptide Nucleic Acid Complexes; *J. Am. Chem. Soc.* (1996) 118:5544-5552.

Traser, S. et al. Syntheses and solution properties of water-soluble poly(p-phenylene)s bearing oligo(ethylene oxide) and trialkylamino side groups; *e-Polymers.* (2002) 32:1-39.

Umek, R.M. et al. Electronic Detection of Nucleic Acids—A Versatile Platform for Molecular Diagnostics; *J. Mol. Diag.* (2001) 3:2:74-84.

Vaishnav, Y.N. and Wong-Staal, F. The Biochemistry of Aids; *Ann. Rev. Biochem.* (1991) 60:577-630.

Varani, G. RNA-Protein Intermolecular Recognition; *Acc. Chem. Res.* (1997) 30:5:189-195.

Vinogradov, S.V. et al. Self-Assembly of Polyamine-Poly(ethylene glycol) Copolymers with Phosphorothioate Oligonucleotides; *Bioconjugate Chem.* (1998) 9:805-812.

Wang, J. et al. Photoluminescence of Water-Soluble Conjugated Polymers: Origin of Enhanced Quenching by Charge Transfer; *Macromolecules.* (2000) 33:5153-5158.

Wang, J. et al. DNA Electrochemical Biosensor for the Detection of Short DNA Sequences Related to the Human Immunodeficiency Virus; *Anal. Chem.* (1996) 68:15:2629-2634.

Isola, N.R. et al. Surface-Enhanced Raman Gene Probe for HIV Detection; *Anal. Chem.* (1998) 70:1352-1356.

Wang, J. Survey and Summary From DNA biosensors to gene chips; *Nucleic Acid Res.* (2000) 28:16:3011-3016.

Wang, J. et al. Dendritic Nucleic Acid Probes for DNA Biosensors; *J. Am. Chem. Soc.* (1998) 120:8281-8282.

Wang, J. et al. Synthesis of AB(BA), ABA and BAB Block Copolymers of *tert*-Butyl Methacrylate (A) and Ethylene Oxide (B); *J. Polym. Sci., Part A: Polym. Chem.* (1992) 30:2251-2261.

Wang, Y. et al. Inte raction of DNA with Cationic Micelles: Effects of Micelle Surface Charge Density, Micelle Shape, and Ionic Strength on Complexation and DNA Collapse; *Langmuir.* (2001) 17:1670-1673.

Waring, M. J. Complex Formation between Ethidium Bromide and Nucleic Acids; *J. Mol. Biol.* (1965) 13:269-282.

Weeks, K.M. et al. Fragments of the HIV-1 Tat Protein Specifically Bind TAR RNA; *Science.* (1990) 249:1281-1285.

Whitcombe, D. et al. Detection of PCR products using self-probing amplicons and fluorescence; *Nat. Biotechnol.* (1999) 17:804-807.

Wolfert, M.A. et al. Polyelectrolyte Vectors for Gene Delivery: Influence of Cationic Polymer on Biophysical Properties of Complexes Formed with DNA; *Bioconjugate Chem.* (1999) 10:993-1004.

Wyman, T.B. et al. Design, Synthesis, and Characterization of a Cationic Peptide that Binds to Nucleic Acids and Perrneabilizes Bilayers; *Biochemistry.* (1997) 36:3008-3017.

Xu, X.H. and Bard, A.J. Immobilization and Hybridization of DNA on an Aluminum(III) Alkanebisphosphonate Thin Film with Electrogenerated Chemiluminescent Detection; *J. Am. Chem. Soc.* (1995) 117:2627-2631.

(56) References Cited

OTHER PUBLICATIONS

Yang, J.S. and Swager, T.M. Fluorescent Porous Polymer Films as TNT Chemosensors: Electronic and Structural Effects; *J. Am. Chem. Soc.* (1998) 120:11864-11873.
Junhui, Z. et al. DNA Based Biosensors; *Biotechnol. Adv.* (1997) 15:43-58.
U.S. Appl. No. 60/202,647, filed May 8, 2000, Whitten.
U.S. Appl. No. 60/226,902, filed Aug. 23, 2000, Whitten.
U.S. Appl. No. 60/230,186, filed Sep. 1, 2000, Phillips.
U.S. Appl. No. 60/237,000, filed Sep. 29, 2000, Bruchez.
U.S. Appl. No. 60/240,216, filed Oct. 13, 2000, Bruchez.
U.S. Appl. No. 60/276,090, filed Mar. 16, 2001, Jones.
U.S. Appl. No. 60/314,094, filed Aug. 23, 2001, Burdick.
U.S. Appl. No. 60/314,101, filed Aug. 23, 2001, Whitten.
Wang et al., "Size-Specific Interactions Between Single- and Double-Stranded Oligonucleotides and Cationic Water-Soluble Oligofluorenes", Adv. Funct. Mater., Jun. 2003, 13(6), 463-467.
Stork et al., "Energy Transfer in Mixtures of Water-Soluble Oligomers: Effect of Charge, Aggregation, and Surfactant Complexation", Adv. Mater., Mar. 2002, 14(5), 361-366.
Leclerc, "Optical and Electrochemical Transducers Based on Functionalized Conjugated Polymers", Adv. Mater., 1999, 11(18), 1491-1498.
Balakin et al., "Conjugates of oligonucleotides with polyaromatic fluorophores as promising DNA probes", Biosensors & Bioelectronics, 1998, 13, 771-778.
Ho et al., "Colorimetric and Fluormetric Detection of Nucleic Acids Using Cationic Polythiophene Derivatives", Angew. Chem. Int. Ed., 2002, 41(9), 1548-1551.
McQuade et al., "Conjugated Polymer-Based Chemical Sensors", Chem. Rev., 2000, 100, 2537-2574.
Chen et al., "Highly sensitive biological and chemical sensors based on reversible fluorescence quenching in a conjugated polymer", PNAS, Oct. 1999, 96(22), 12287-12292.
Liu et al., "Effect of Chromophore-Charge Distance in the Energy Transfer Properties of Water-Soluble Conjugated Oligomers", J. Am. Chem. Soc., 2003, 125, 6705-6714.
Gaylord et al., "DNA detection using water-soluble conjugated polymers and peptide nucleic acid probes", PNAS, Aug. 2002, 99(17), 10954-10957.
Bronich et al., "Recognition of DNA Topology in Reactions between Plasmid DNA and Cationic Copolymers", J. Am. Chem. Soc., Sep. 2000, 122(35), 8339-8343.
Chen et al., "Tuning the Properties of Conjugated Polyelectrolytes through Surfactant Complexation", J. Am. Chem. Soc., 2000, 122, 9302-9303.
Gaylord et al., "Water-Soluble Conjugated Oligomers: Effect of Chain Length and Aggregation on Photoluminescene-Quenching Efficiencies", J. Am. Chem. Soc., 2001, 123, 6417-6418.
Hong et al., "Water-Soluble Oligmer Dimers Based on Paracyclophane: A New optical Platform for Fluorescent Sensor Applications", J. Am. Chem. Soc., 2002, 124, 11868-11869.
Gaylord et al., "DNA Hybridization Detection with Water-Soluble Conjugated Polymers and Chromophore-Labeled Single-Stranded DNA", J. Am. Chem. Soc., 2003, 125, 896-900.
Zhou et al., "Fluorescent Chemosensors Based on Energy Migration in Conjugated Polymers: The Molecular Wire Approach to Increased Sensitivity", J. Am. Chem. Soc., 1995, 117, 12593-12602.
Zhou et al., "Methodology for Enhancing the Sensitivity of Fluorescent Chemosensors: Energy Migration in Conjugated Polymers", J. Am. Chem. Soc., 1995, 117, 7017-7018.
Hawkins et al., "Incorporation of a fluorescent guanosine analog into oligonucleotides and its application to a real time assay for the HIV-1 integrase 3'-processing reaction", Nucleic Acids Research, 1995, 23(15), 2872-2880.
Cardullo et al., "Detection of Nucleic Acid Hybridization by Nonradiative Fluorescence Resonance Energy Transfer", Proc. Natl. Acad. Sci. USA, Dec. 1998, 85, 8790-8794.
Gallot et al., "Poly(L-lysine) containing azobenzene units in the side chains: influence of the degree of substitution on liquid crystalline structure and thermotropic behaviour", Liquid Crystals, 1997, 23(1), 137-146.
Wang et al., "Biosnesors from conjugated polyelectrolyte complexes", PNAS, Jan. 2002, 99(1), 49-53.
Liu et al., "Methods for strand-specific DNA detection with cationic conjugation polymers suitable for incorporation into DNA chips and microarrays", PNAS Early Edition, Dec. 2004, p. 1-5.
Vehse et al., "Light Amplification by Optical Excitation of a Chemical Defect in a Conjugated Polymer", Adv. Mater., Jun. 2004, 16(12), 1001-1004.
Liu et al., "Shape-Adapable Water-Soluble Conjugated Polymers", J. Am. Cham. Soc., 2003, 125, 13306-13307.
Liu et al., "Interpolyelectrolyte Complexes of Conjugated Copolymers and DNA: Platforms for Multicolor Biosensors", J. Am. Chem. Soc., 2004, 126, 1942-1943.
Huang et al., "High-Efficiency, Evironment-Friendly Electroluminescent Polymers with Stable High Work Function Metal as a Cathode: Green- and Yellow-Emitting Conjugated Polyfluorene Polyelectrolytes and Their Neutral Precursors", J. Am. Chem. Soc., 2004, 126, 9845-9853.
Service, "DNA Analysis: Microchip Arrays Put DNA on the Spot", The American Association for the Advancement of Science, Oct. 1998, 282(5388), 396-399.
Southern, "DNA chips: analysing sequence by hybridization to oligonucleotides on a large scale", TIG, Mar. 1996, 12(3), 110-115.
Epstein et al., "Microarray technology—enhanced versatility, persistent challenge", Current Opinion in Biotechnology, 2000, 11, 36-41.
Heeger et al., "Making Sense of polymer-based biosensors", PNAS, Oct. 1999, 96(22), 12219-12221.
Patel et al., "Energy transfer analysis of Fos-Jun dimerization and DNA binding", Proc. Natl. Sci. USA, Jul. 2994, 91, 7360-7364.
Lohse et al., "Fluorescein-Conjugated Lysine Monomers for Solid Phase Synthesis of Fluorescents Peptides and PNA Oligomers", Bioconjugate Chem., 1997, 8, 503-509.
Smith et al., "The synthesis of oligonucleotides containing an aliphatic amino group at the 5' terminus: synthesis of fluorescent DNA primers for use in DNA sequence analysis", Nucleic Acids Research, 1985, 13(7) 2399-2412.
Wintermeyer et al., "Fluorescent Derivatives of Yeast tRNA(TM)", Eur. J. Biochem., 1979, 98, 465-475.
Lipshutz et al., "High density synthetic oligonucleotide arrays", Nature Genetics Supplement, Jan. 1999, 21, 20-24.
Nilsson et al., "Chip solution detection of DNA hybridization using a luminescent zwitterionic polythiophene derivative", Nature Materials, Jun. 2003, 2, 419-424 (Supplementary Information pp. 1-2).
Dore et al., "Fluorescent Polymeric Transducer for the Rapid, Simple, and Specific Detection of Nucleic Acids at the Zeptomole Level", J. Am. Chem. Soc., 2004, 126, 4240-4244.
Ranade et al., "High-Throughput Genotyping with Single Nucleotide Polymorphisms", Genone Research, 2001, 11, 1262-1268.
Schork et al., "Single nucleotide polymorphisms and the furture if genetic epidemiology", Clin. Genet., 2000, 58, 250-264.
Wang et al., "Optically Amplified RNA-Protein Detection Methods Using Light-Harvesting Conjugated Polymers", Adv. Mater., Sep. 2003, 15(17), 1425-1428.
Liu et al., "Homogeneuos Fluorescents-Based DNA Detection with Water-Soluble Conjugated Polymers", Chem. Mater., 2004, 16, 4467-4476.
Wolcott, "Advances in Nucleic Acid-Based Detection Methods", Clinical Microbiology Reviews, Oct. 1992, 5(4), 370-386.
Umek et al., "Electronic Detection of Nucleic Acids, A Versatile Platform for Molecular Diagnostics", Journal of Molecular Diagnostics, May 2001, 3(2), 74-84.
Stevens et al., "Exciton dissociation mechanisms in the polymeric semiconductors poly(9,9-dioctylfluorene) and poly(9,9-dioctylfluorene-co-benzothiadiazole)", Physical Review B, Apr. 2001, 63, 1-18.
Wang, "Survey and Summary From DNA biosensors to gene chips", Nucleic Acids Research, 2000, 28(16), 3011-3016.

(56) References Cited

OTHER PUBLICATIONS

Beier et al., "Versatile derivatisation of solid support media for covalent bonding on DNA-microchips", Nucleic Acids Research, 1999, 27(9), 1970-1977.

Ajayaghosh, et al., "A Novel Approach Towards Low Optical Band Gap Polysquarines," Organic Letters, Aug. 9, 2001, 3(16), 2595-2598.

Bazan, et al., "Characterisation of tectoRNA Assembly with Cationic Conjugated Polymers," Journal of the American Chemical Society, Apr. 7, 2004, 126(13), 4076-4077.

Brandt, et al., "Peptide Nucleic Acids on Microarrays and Other Biosensors," Trends in Biotechnology, Dec. 2004, 22(12), 617-622.

Gaylord, et al., "SNP Detection Using Peptide Nucleic Acid Probes and Conjugated Polymers: Applications in Neurodegenerative Disease Identification," PNAS, 2005, 102(1), 34-39.

Glazer, A. N. et al., "Stable Dye-DNA Intercalation Complexes as Reagents for High Sensitivity Fluorescence Detection," Nature, Oct. 29, 1992, 359, 859-861.

Huang, et al., "Novel Electroluminescent Conjugated Polyelectrolytes Based on Polyfluorene," Chemistry of Materials, Jan. 28, 2004, 16(4), 708-716.

Liu, et al., "Blue-Light-Emitting Cationic Water-Soluble Polyfluorene Derivatives with Tunable Quaternization Degree," Macromolecules, May 2002, 35(13), 4975-4982.

Stewart, et al., "Chromophore-Labeled Dendrons as Light Harvesting Antennae," J. Am. Chem. Soc., 1996, 118(18), 4354-4360.

Sun, et al., "Application of Cationic Conjugated Polymers in Microarrays Using Label-Free DNA Targets," Nature Protocols, 2007, 2(9), 1-4.

Wang, "Fluorescein Provides a Resonance Gate for FRET from Conjugated Polymers to DNA Intercalated Dyes," JACS, 2004, 126(7), 5446-5451.

Wang, et al., "Solvent-Dependant Aggregation of a Water-Soluble Poly(fluorene) Controls Energy Transfer to Chromophore-Labeled DNA," Chem. Comm., R. Soc. Chem., 2004, 2508-2509.

Weiler, et al., "Hybridization Based DNA Screening on Peptide Nucleic Acid (PNA) Oligomer Arrays," Nucleic Acids Research, 1997, 25(14), 2792-2799.

* cited by examiner

SEQUENCE LISTING

```
<160> NUMBER OF SEQ ID NOS: 6

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Ala Arg Lys Lys Arg Arg Gln Arg Arg Arg Ala Ala Ala Cys
 1               5                  10                  15

<210> SEQ ID NO 2
<211> LENGTH: 31
<212> TYPE: RNA
<213> ORGANISM: Human immunodeficiency virus type 1
```

```
<400> SEQUENCE: 2
ggccagaucu gagccuggga gcucucuggc c                              31

<210> SEQ ID NO 3
<211> LENGTH: 28
<212> TYPE: RNA
<213> ORGANISM: Human immunodeficiency virus type 1

<400> SEQUENCE: 3
ggccagagag ccugggagcu cucuggcc                                  28

<210> SEQ ID NO 4
<211> LENGTH: 17
<212> TYPE: PRT
<213> ORGANISM: Influenza A virus

<400> SEQUENCE: 4

Asp Pro Asn Asn Met Asp Lys Ala Val Lys Leu Tyr Arg Lys Leu Lys
 1               5                  10                  15
Arg

<210> SEQ ID NO 5
<211> LENGTH: 22
<212> TYPE: PRT
<213> ORGANISM: Homo sapiens

<400> SEQUENCE: 5

Met Arg Gly Gly Asn Phe Arg Gly Gly Ala Pro Gly Asn Arg Gly Gly
 1               5                  10                  15
Tyr Asn Arg Arg Gly Asn
            20

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Lys Pro Arg Pro Pro Arg Pro Leu Pro Val Ala Cys
 1               5                  10
```

US 8,993,335 B2

METHODS FOR DETECTION AND ANALYSIS OF POLYNUCLEOTIDE-BINDING PROTEIN INTERACTIONS

CROSS REFERENCE TO RELATED APPLICATIONS

This application claims the benefit of U.S. Provisional Application No. 60/447,860, filed Feb. 13, 2003, which is hereby incorporated by reference in its entirety.

STATEMENT REGARDING FEDERALLY SPONSORED RESEARCH

Work leading to this invention was performed under grant number GM62958-01 from the National Institutes of Health, grant number DMR-0097611 from the National Science Foundation and grant number N00014-1-1-0239 from the Office of Naval Research. The U.S. Government may have limited rights in this invention.

TECHNICAL FIELD

This invention relates to methods, articles and compositions for the detection and analysis of polynucleotides in a sample.

BACKGROUND OF THE INVENTION

Methods permitting polynucleotide analysis in real time and with high sensitivity are of great scientific and economic interest.[1,2,3] Their applications include medical diagnostics, identification of genetic mutations, gene delivery monitoring and specific genomic techniques.[4] Cationic organic dyes, such as ethidium bromide and thiazole orange, emit when intercalated into the grooves of double strand DNA (dsDNA), and serve as direct DNA hybridization probes, but lack sequence specificity.[5,6] Energy/electron transfer chromophore pairs for strand specific assays exist, but require chemical labeling of two nucleic acids, or dual modification of the same altered strand (for example, molecular beacons).[7,8] Difficulties in labeling two DNA sites result in low yields, high costs and singly labeled impurities, which lower detection sensitivity.[9]

There is a need in the art for methods of detecting and analyzing particular polynucleotides in a sample, and for compositions and articles of manufacture useful in such methods.

SUMMARY OF THE INVENTION

Methods, compositions and articles of manufacture for detecting and assaying a target polynucleotide in a sample are provided.

In a first embodiment, a sample suspected of containing the target polynucleotide is contacted with a polycationic multichromophore and a sensor polynucleotide binding protein (PBP) that can bind to the target polynucleotide. The sensor PBP comprises a signaling chromophore. Without wishing to be bound by theory, in the presence of target polynucleotide in the sample, the signaling chromophore is believed to be brought into proximity with the cationic multichromophore by utilizing electrostatic interactions with the backbone of the target polynucleotide bound to the sensor PBP (see FIG. 1). The signaling chromophore can then acquire energy from the excited polycationic multichromophore and emit light which can be detected. The target polynucleotide can be analyzed as it occurs in the sample, or can be amplified prior to or in conjunction with analysis.

Solutions are provided comprising reagents useful for performing the methods of the invention, as are kits containing such reagents. The methods can be used in multiplex settings where a plurality of different sensor PBPs are used to assay for a plurality of different target polynucleotides. The methods can optionally be performed on a surface, for example using a surface-associated polycationic multichromophore; the surface can be a sensor. The methods can also be provided in homogeneous formats. The methods and articles described herein can be used as alternatives to other techniques for detecting polynucleotides.

BRIEF DESCRIPTION OF THE DRAWINGS

The patent or application file contains at least one drawing executed in color. Copies of this patent or patent application publication with color drawings will be provided by the Patent and Trademark Office upon request and payment of the necessary fee.

DETAILED DESCRIPTION OF THE INVENTION

Figure 1:
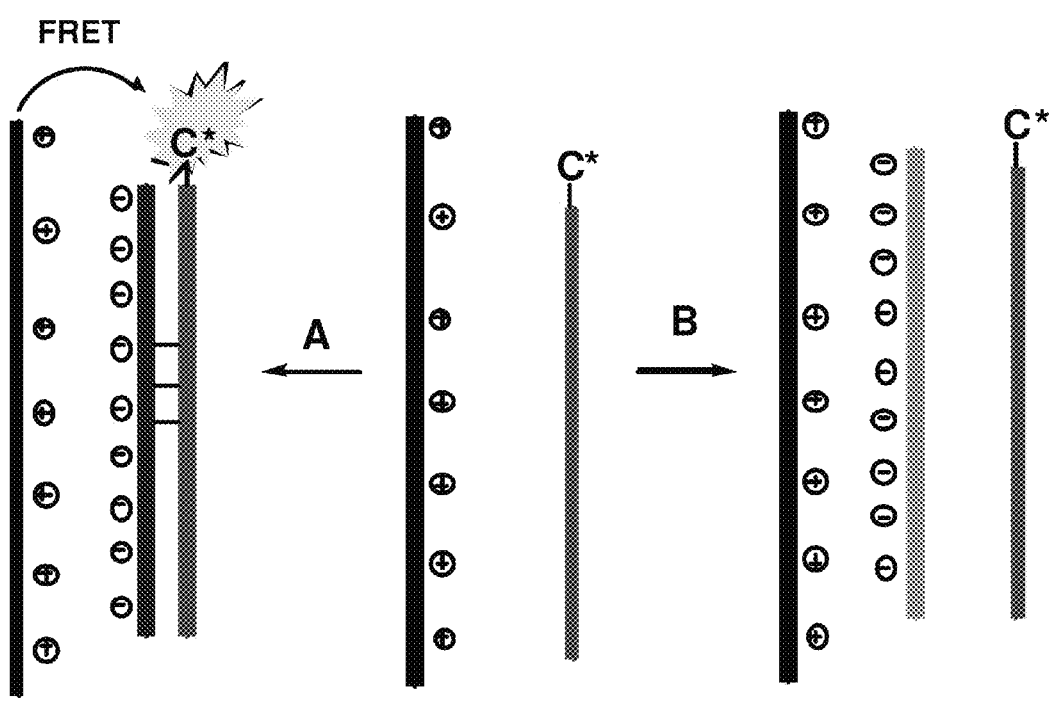
FIG. 1 depicts the method of the invention, employing a polycationic polymer as the light-harvesting multichromophore. A sensor PBP (PBP-C*) comprises a signaling chromophore and a binding specificity for the target polynucleotide of interest. Upon contacting the target polynucleotide in a sample, the polycationic multichromophore is brought into proximity with the signaling chromophore by virtue of its own interactions with the target polynucleotide. Excitation of the multichromophore then produces light emission from the signaling chromophore.

Present technologies for DNA and RNA sensors (including "gene-chips" and "DNA-chips") depend on the covalent attachment of fluorescent tags (lumophores) to single strands of DNA. Most of these sensors are forced to rely on the labeling of the analyte sample, with unavoidable problems resulting from variations in the efficiency of the labeling reaction from sample to sample, requiring complex cross-calibrations. Other systems rely on the "molecular beacon" approach, requiring the attachment of lumophores and quenchers to precisely engineered sequences.

A method for polynucleotide analysis is provided comprising contacting a sample with at least two components; (a) a light harvesting, luminescent multichromophore system such as, for example, a conjugated polymer, semiconductor quantum dot or dendritic structure that is water soluble, and (b) a sensor PBP conjugated to a luminescent signaling chromophore ("PBP-C*"). The emission of a wavelength of light characteristic of the signaling chromophore-C* upon excitation of the multichromophore indicates the presence in solution of the target polynucleotide. By using multiple different sensor PBPs, each with a different base sequence and a different signaling chromophore (PBP1-C1*, PBP2-C2*, PBP3-C3*, PBP4-C4*, etc), multiple different polynucleotides can be independently detected and assayed.

The light harvesting chromophore and the signaling chromophore (C*) are chosen so that the absorption bands of the two chromophores have minimal overlap and so that the luminescent emission spectra of the two species are at different wavelengths. When prepared in aqueous solution, the light harvesting luminescent multichromophore system is positively charged, or cationic, and is preferably polycationic (for example a polycationic conjugated polyelectrolyte). The sensor PBP and multichromophore are chosen such that there is minimal interaction between them in the absence of target. Upon addition of a target polynucleotide that can bind to the sensor PBP, the target polynucleotide forms a complex with the sensor PBP. Because the target polynucleotide is negatively charged, the sensor PBP is brought into association with the polycationic multichromophore, permitting energy transfer from the polycationic multichromophore to the signaling chromophore, for example via the Förster energy transfer mechanism. When a polynucleotide that does not bind to the sensor PBP is added, complexation between the multichromophore and the sensor PBP does not occur. Because the average distance between the polycationic multichromophore and the signaling chromophore is too large for effective energy transfer in the absence of such complex formation, there is little or no emission from the signaling chromophore. The overall scheme serves to detect the presence of the target polynucleotide in the test solution.

In addition to the described method, the invention provides a predominantly aqueous solution comprising at least two components; (a) a cationic multichromophore, and (b) a "sensor PBP" (PBP-C*) comprising a polynucleotide binding protein conjugated to a signaling chromophore.

As demonstrated in the Examples, the optical amplification provided by a water soluble multichromophore such as a conjugated polymer can be used to detect polynucleotide binding to a PBP sensor. The amplification can be enhanced by using higher molecular weight water soluble conjugated polymers or other structures as the polycationic multichromophore as described herein. The invention can be provided in a homogeneous format that utilizes the ease of fluorescence detection methods. The invention can be used to detect amplified target polynucleotides or, because of the large signal amplification, as a stand alone assay, without need for polynucleotide amplification.

Unique advantages of the invention over present gene-chip technology thus include circumvention of the requirement to first label each sample to be analyzed by covalent coupling of lumophores or chromophores to the polynucleotides contained in or derived from the sample prior to analysis. Those coupling methods have inherent difficulties in reproducibility of coupling efficiency and result in the need for cross-calibration from sample to sample.

The inventions described herein are useful for any assay in which a sample can be interrogated regarding a target polynucleotide. Typical assays involve determining the presence of the target polynucleotide in the sample or its relative amount, or the assays may be quantitative or semi-quantitative.

The methods of the invention can all be performed in multiplex formats. A plurality of different sensor PBPs can be used to detect corresponding different target polynucleotides in a sample through the use of different signaling chromophores conjugated to the respective sensor PBPs. Multiplex methods are provided employing 2, 3, 4, 5, 10, 15, 20, 25, 50, 100, 200, 400 or more different sensor PBPs which can be used simultaneously to assay for corresponding different target polynucleotides.

The methods can be performed on a substrate, as well as in solution, although the solution format is expected to be more rapid due to diffusion issues. Thus the assay can be performed, for example, in an array format on a substrate, which can be a sensor. This can be achieved by anchoring or otherwise incorporating an assay component onto the substrate, for example the sensor PBP, the polycationic multichromophore, or both. These substrates may be surfaces of glass, silicon, paper, plastic, or the surfaces of optoelectronic semiconductors (such as, but not confined to, indium-doped gallium nitride or polymeric polyanilines, etc.) employed as optoelectronic transducers. The location of a given sensor PBP may be known or determinable in an array format, and the array format may be microaddressable or nanoaddressable.

Before the present invention is described in further detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a target polynucleotide" includes a plurality of target polynucleotides, reference to "a signaling chromophore" includes a plurality of such chromophores, reference to "a sensor PBP" includes a plurality of sensor PBPs, and the like. Additionally, use of specific plural references, such as "two," "three," etc., read on larger numbers of the same subject unless the context clearly dictates otherwise.

Terms such as "connected," "attached," and "linked" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are for the purpose of describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

Definitions

In describing the present invention, the following terms will be employed, and are intended to be defined as indicated below.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. These terms refer only to the primary structure of the molecule. Thus, the terms includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide.

Whether modified or unmodified, the target nucleotide should have a polyanionic backbone, preferably a sugar-phosphate backbone, of sufficient negative charge to electrostatically interact with the polycationic multichromophore in the methods described herein, although other forces may additionally participate in the interaction. The sensor PBP is a polynucleotide binding protein which minimally interacts with the multichromophore in the absence of target. Suitable binding conditions for a given assay format can be determined by one of skill in the art; nonlimiting parameters which may be adjusted include concentrations of assay components, pH, salts used and their concentration, ionic strength, temperature, etc.

More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing a phosphate or other polyanionic backbone, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3'P5' phosphoramidates, 2'-O-alkyl-substituted RNA, double- and single-stranded DNA, as well as double- and single-stranded RNA, and hybrids thereof including for example hybrids between DNA and RNA, and also include known types of modifications, for example, labels, alkylation, "caps," substitution of one or more of the nucleotides with an analog, internucleotide modifications such as, for example, those with negatively charged linkages (e.g., phosphorothioates, phosphorodithioates, etc.), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide; preferably the polynucleotide does not comprise abasic sites. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'-H and C6-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described in U.S. Pat. No. 5,780,610 to Collins et al. Other nonnatural base pairs may be synthesized by the method described in Piccirilli et al. (1990) Nature 343:33-37 for the synthesis of 2,6-diaminopyrimidine and its complement (1-methylpyrazolo-[4,3]pyrimidine-5,7-(4H,6H)-dione). Other such modified nucleotidic units which form unique base pairs are known, such as those described in Leach et al. (1992) J. Am. Chem. Soc. 114:3675-3683 and Switzer et al., supra.

"Complementary" or "substantially complementary" refers to the ability to hybridize or base pair between nucleotides or nucleic acids, such as, for instance, between a sensor polynucleotide binding protein and a target polynucleotide. Complementary nucleotides are, generally, A and T (or A and U), or C and G. Two single-stranded polynucleotides are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide or PNA will hybridize under selective hybridization conditions to its complement. Typically, selective hybridization will occur when there is at least about 65% complementary over a stretch of at least 14 to 25 bases, preferably at least about 75%, more preferably at least about 90% complementary. See, M. Kanehisa Nucleic Acids Res. 12:203 (1984).

"Preferential binding" or "preferential hybridization" refers to the increased propensity of one member of a binding pair to bind to its binding partner as compared to another component of the sample.

Hybridization conditions will typically include salt concentrations of less than about 1M, more usually less than about 500 mM and preferably less than about 200 mM. In the case of hybridization between a peptide nucleic acid and a polynucleotide, the hybridization can be done in solutions containing little or no salt. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multiplexing" herein refers to an assay or other analytical method in which multiple analytes can be assayed simultaneously.

"Optional" or "optionally" means that the subsequently described event or circumstance may or may not occur, and that the description includes instances where the event or circumstance occurs and instances in which it does not.

A polynucleotide sensor is provided comprising two components; (a) a light harvesting, luminescent water-soluble polycationic multichromophore, such as a conjugated polymer, oligomer or dendritic molecule; (b) a sensor polynucleotide binding protein or a binding fragment thereof labeled with a luminescent signaling chromophore (PBP-C*). The binding of PBP-C* to a target polynucleotide results in the formation of a complex of sufficient negative charge to interact with the polycationic multichromophore. Electrostatic (and hydrophobic) interactions with the cationic light harvesting molecule bring the signaling chromophore (C*) in close proximity to the light harvesting molecule. Excitation of the light harvesting molecule at the appropriate frequency results in energy transfer to the signaling chromophore. Emission from C* confirms binding between PBP-C* and the target polynucleotide. If the sensor-target interactions are specific, then C* emission corresponds to the presence of a specific DNA or RNA sequence in solution.

A schematic of the sensor operation is shown in FIG. 1. In aqueous solution, there is minimal interaction between the cationic light harvesting molecules (shown in black) and the probe PBP-C* (shown in red). The PBP and the light harvesting molecule are chosen so that they do not interact significantly in the absence of target. Upon addition of a sample containing polynucleotides, two situations can take place. Situation A shows the results of the signaling PBP-C* binding to the target polynucleotide (in blue). Under these conditions the negatively charged DNA-PBP-C* or RNA-PBP-C* complex associates by multiple electrostatic interactions with the positively charged light harvesting conjugated molecules. The ensuing close proximity results in energy transfer from the light harvesting conjugated molecules to the signaling chromophore of PBP-C*, for example via the Förster energy transfer mechanism.[10,11] The emission of light with wavelength characteristic of signaling C* indicates the recognition between the protein and RNA or DNA. When a polynucleotide is present which does not interact with the PBP-C* (shown in green), the PBP-C* is not adjacent to a negatively charged macromolecule and the distance between the cationic light harvesting molecule and C* is too large for energy transfer (situation B).

As a specific working example of the sensor we have used the following two components: (a) a light harvesting, luminescent water-soluble conjugated molecules, such as conjugated polymers and conjugated oligomers; (b) a 16-residue peptide labeled with a luminescent signaling chromophore at the N-terminus (Tat-C*). The light harvesting molecules and the signaling chromophore (C*) are chosen so that the luminescent emission spectra of the two species are at different wavelengths and so that the absorption of C* overlaps the emission of the light harvesting species. Upon addition of TAR RNA, the signaling peptide Tat-C* specifically binds with TAR RNA. The negatively charged TAR RNA/Tat-C* complex then associates with the positively charged light harvesting conjugated molecules (situation A). The ensuing close proximity results in energy transfer from the light harvesting conjugated molecules to the signaling chromophore of Tat-C*. The emission of light with wavelength characteristic of signaling Tat-C* indicates the presence of HIV TAR RNA. When an RNA which does not interact with Tat is used, the RNA and the cationic molecule interact, however there is no energy transfer to C*.

Developing reliable technologies for detecting human immunodeficiency virus type 1 (HIV-1) is of significant clinical interest.[12,13,14,15] The traditional detection technologies for HIV infection is an ELISA test for the HIV antibody, in which viral antigens are adsorbed onto a solid phase.[22,16] A western blot assay coupling electrophoretic separation with radioisotopic detection is also common for this task.[22,17] The drawbacks of these technologies include complex instrumentation, the time required for the assay and complications caused by the short half-life and hazardous nature of radiolabeled probes. Simple, high sensitive, specific and real-time methods are highly desired for detecting HIV virus.

The transactivation responsive element RNA sequence (TAR) of HIV is expressed at high levels by virally infected cells.[18] The ability to conveniently monitor TAR RNA in real-time as described herein provides a viable method for the rapid detection for the presence of the HIV virus. Extensive studies demonstrate that the transactivator protein (Tat) binds the TAR RNA with great specificity and approximately 1 nM affinity, to form a stable, well-defined complexes.[19,20,21] The specific binding of Tat to TAR RNA thus triggers signal transduction for the clinically relevant real-time detection of HIV using the methods described herein.

The working examples demonstrate a novel HIV bio-optical sensor which couples the specificity of Tat peptide binding and folding to TAR RNA with the large optical amplification of conjugated polymers and oligomers. The HIV RNA sensor comprises two components: (a) light harvesting, luminescent water-soluble conjugated molecules, such as conjugated polymers and conjugated oligomers; (b) a 16-residue peptide being labeled with a luminescent signaling chromophore at N-terminus (Tat-C*). The binding of the probe peptide and luminescent conjugated molecules to the TAR RNA results in the formation of a complex and introduces energy transfer from conjugated molecules to Tat-C*. The emission of light with wavelength characteristic of the signaling Tat-C* indicates the presence of HIV-1 TAR RNA.

Figure 2:
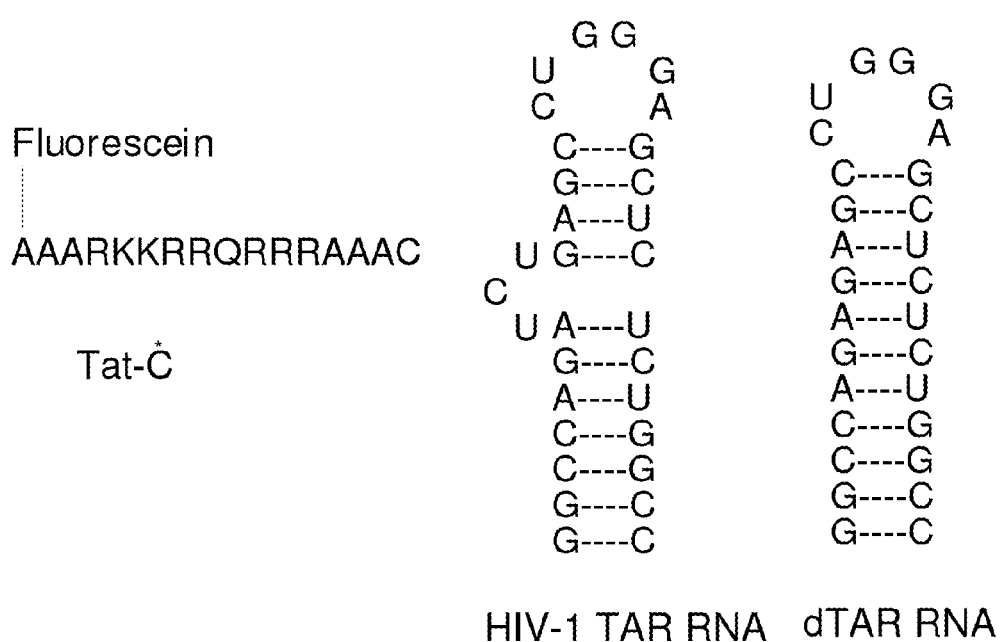
FIG. 2 depicts the molecular structures of Tat-C* (SEQ ID NO: 1) used in the working examples (where C* is fluorescein), TAR RNA (SEQ ID NO: 2) and dTAR RNA (SEQ ID NO: 3).

As demonstrated in the Examples, the optical amplification of water soluble conjugated molecules can be used to detect the presence of HIV TAR RNA. This invention can be used in a homogeneous format that utilizes the ease of fluorescence detection methods and the specific binding behavior found in protein-polynucleotide interactions such as Tat-TAR RNA interactions and provides the ability to detect TAR RNA in real time. The structures of Tat peptide, TAR RNA and dTAR RNA used in the working examples are shown in FIG. 2 (with amino acids shown in single letter code for Tat-C*).

As shown by Förster[22], dipole-dipole interactions lead to long-range resonance energy transfer (FRET) from a donor chromophore to an acceptor chromophore. The energy transfer efficiency (E) is proportional to $1/r^6$, where r is the donor-acceptor distance, and the overlap integral, as shown in Equation 1.

$$E \propto \frac{1}{r^6} \cdot \int_0^\infty F_D(\lambda)\varepsilon_A(\lambda)\lambda^4 d\lambda \quad (1)$$

The distance requirement for energy transfer in the methods described herein will be controlled by the interactions in FIG. 1. The overlap integral expresses the spectral overlap between the emission of the donor and the absorption of the acceptor[23]. As exemplified herein, the components of the sensor can be chosen so that their optical properties meet this requirement.

The Sample

The portion of the sample comprising or suspected of comprising the target polynucleotide can be any source of biological material which comprises polynucleotides that can be obtained from a living organism directly or indirectly, including cells, tissue or fluid, and the deposits left by that organism, including viruses, mycoplasma, and fossils. The sample may comprise a target polynucleotide prepared through synthetic means, in whole or in part. Typically, the sample is obtained as or dispersed in a predominantly aqueous medium. Non-limiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant library comprising polynucleotide sequences.

The sample can be a positive control sample which is known to contain the target polynucleotide or a surrogate therefor. A negative control sample can also be used which, although not expected to contain the target polynucleotide, is suspected of containing it (via contamination of one or more of the reagents) or another component capable of producing a false positive, and is tested in order to confirm the lack of contamination by the target polynucleotide of the reagents used in a given assay, as well as to determine whether a given set of assay conditions produces false positives (a positive signal even in the absence of target polynucleotide in the sample).

The sample can be diluted, dissolved, suspended, extracted or otherwise treated to solubilize and/or purify any target polynucleotide present or to render it accessible to reagents which are used in an amplification scheme or to detection reagents. Where the sample contains cells, the cells can be lysed or permeabilized to release the polynucleotides within the cells. One step permeabilization buffers can be used to lyse cells which allow further steps to be performed directly after lysis, for example a polymerase chain reaction.

The Target Polynucleotide and Amplification Products Produced Therefrom

The target polynucleotide can be single-stranded, double-stranded, or higher order, and can be linear or circular. Exemplary single-stranded target polynucleotides include mRNA, rRNA, tRNA, hnRNA, ssRNA or ssDNA viral genomes, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phage, and viroids. The target polynucleotide can be prepared synthetically or purified from a biological source. The target polynucleotide may be purified to remove or diminish one or more undesired components of the sample or to concentrate the target polynucleotide. Conversely, where the target polynucleotide is too concentrated for the particular assay, the target polynucleotide may be diluted.

Following sample collection and optional nucleic acid extraction, the nucleic acid portion of the sample comprising the target polynucleotide can be subjected to one or more preparative reactions. These preparative reactions can include in vitro transcription (IVT), labeling, fragmentation, amplification and other reactions. mRNA can first be treated with reverse transcriptase and a primer to create cDNA prior to detection and/or amplification; this can be done in vitro with purified mRNA or in situ, e.g. in cells or tissues affixed to a slide. Nucleic acid amplification increases the copy number of sequences of interest such as the target polynucleotide. A variety of amplification methods are suitable for use, including the polymerase chain reaction method (PCR), the ligase chain reaction (LCR), self sustained sequence replication (3SR), nucleic acid sequence-based amplification (NASBA), the use of Q Beta replicase, reverse transcription, nick translation, and the like.

Where the target polynucleotide is single-stranded and is to be amplified, the first cycle of amplification forms a primer extension product complementary to the target polynucleotide. If the target polynucleotide is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide is typically amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity which can copy the target polynucleotide can be used, including DNA polymerases, RNA polymerases, reverse transcriptases, enzymes having more than one type of polymerase activity, and the enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB-D DNA polymerases; RNA-polymerases such as *E. coli*, SP6, T3 and T7 RNA polymerases; and reverse transcriptases such as AMV, M-MuLV, MMLV, RNAse H-MMLV (SuperScript® polymerase), SuperScript® II polymerase, ThermoScript® polymerase, HIV-1, and RAV2 reverse transcriptases. All of these enzymes are commercially available. Exemplary polymerases with multiple specificities include RAV2 and Tli(exo-)polymerases. Exemplary thermostable polymerases include Tub, Tag, Tth, Pfx, Pfu, Tsp, Tfl, Tli and *Pyroccoccus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

Amplified target polynucleotides may be subjected to post amplification treatments. For example, in some cases, it may be desirable to fragment the target polynucleotide prior to hybridization in order to provide segments which are more readily accessible. Fragmentation of the nucleic acids can be carried out by any method producing fragments of a size useful in the assay being performed; suitable physical, chemical and enzymatic methods are known in the art.

An amplification reaction can be performed under conditions which allow the sensor PBP to bind to the amplification product during at least part of an amplification cycle. When the assay is performed in this manner, real-time detection of this hybridization event can take place by monitoring for a change in light emission from the signaling chromophore that occurs upon such hybridization during the amplification scheme.

The Polycationic Multichromophore

Light harvesting multichromophore systems have been demonstrated to be efficient light absorbers by virtue of the multiple chromophores they comprise. Examples include, but are not limited to, conjugated polymers, aggregates of conjugated molecules, luminescent dyes attached via side chains to saturated polymers, semiconductor quantum dots and dendritic structures. For example, each repeat unit on a conjugated polymer can be considered as a contributing chromophore, quantum dots are made up of many atoms, a saturated polymer can be functionalized with many luminescent dye molecules on side chains, and dendrimers can be synthesized containing many covalently bonded individual chromophores. Attachment of chromophore assemblies onto solid supports, such as polymer beads or surfaces, can also be used for light harvesting.

Light harvesting multichromophore systems can efficiently transfer energy to nearby luminescent species (e.g., "signaling chromophores"). Mechanisms for energy transfer include, for example, resonant energy transfer (Förster (or fluorescence) resonance energy transfer, FRET), quantum charge exchange (Dexter energy transfer) and the like. Typically, however, these energy transfer mechanisms are relatively short range; that is, close proximity of the light harvesting multichromophore system to the signaling chromophore is required for efficient energy transfer. Under conditions for efficient energy transfer, amplification of the emission from the signaling chromophore occurs when the overall absorptive ability of the multichromophore exceeds that of the signaling chromophore, for example when the number of individual chromophores in the light harvesting multichromophore system is large; that is, the emission from the signaling chromophore is more intense when the incident light (the "pump light") is at a wavelength which is absorbed by the light harvesting multichromophore system than when the signaling chromophore is directly excited by the pump light.

Conjugated polymers (CPs) are characterized by a delocalized electronic structure and can be used as highly responsive optical reporters for chemical and biological targets.[24,25]

Exemplary polycationic multichromophores are shown below, where the cationic water soluble conjugated molecules are polymer 1 (where n=2-100,000), oligomer 1 and oligomer 2. This specific molecular structure is not critical; any water soluble cationic light harvesting molecules can be used.

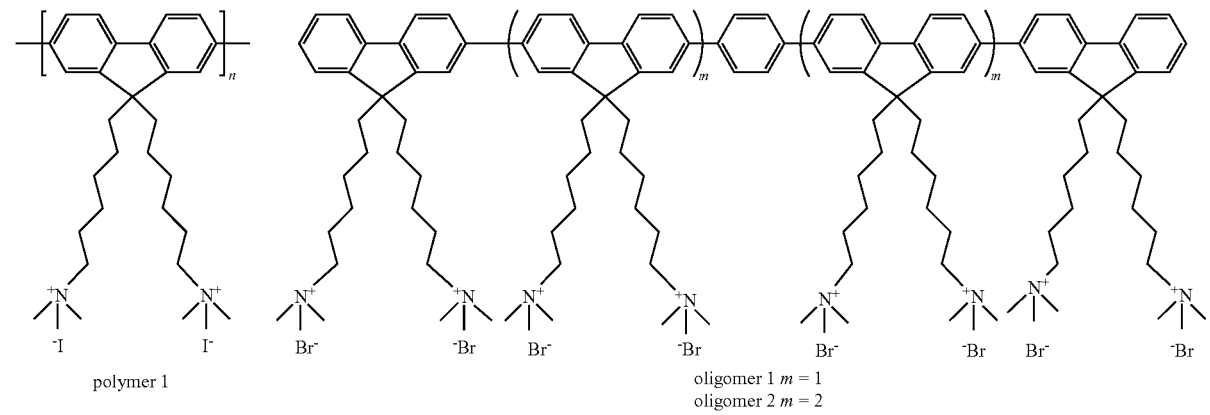

polymer 1 oligomer 1 $m = 1$
oligomer 2 $m = 2$

Because the effective conjugation length is substantially shorter than the length of the polymer chain, the backbone contains a large number of conjugated segments in close proximity. Thus, conjugated polymers are efficient for light harvesting and enable optical amplification via Förster energy transfer.[26] Water-soluble CPs show exceptional fluorescence quenching efficiencies in the presence of oppositely charged acceptors and are of particular interest for transduction of biological recognition events.[27,28]

Spontaneous interpolymer complexation between cationic polyelectrolytes and DNA has been described and is largely the result of cooperative electrostatic forces.[29,30,31] Hydrophobic interactions between aromatic polymer units and DNA bases were also recently recognized.[32,33] The free energy of polyelectrolyte/DNA interactions is controlled by the structure of the participating species used in conjunction with solution variables such as pH, ionic strength, and temperature.[34] The strength and specificity of these interactions has recently been coordinated to recognize the tertiary structure of plasmid DNA.[35]

The multichromophores used in the present invention are polycationic so that they can interact with a target polynucleotide electrostatically and thereby bring a signaling chromophore on an uncharged sensor PBP into energy-receiving proximity by virtue of binding between the sensor PBP and the target polynucleotide. Any polycationic multichromophore that can absorb light and transfer energy to a signaling chromophore on a sensor PBP can be used in the methods described. Exemplary multichromophores which can be used include conjugated polymers, saturated polymers or dendrimers incorporating multiple chromophores in any viable manner, and semiconductor nanocrystals (SCNCs). The conjugated polymers, saturated polymers and dendrimers can be prepared to incorporate multiple cationic species or can be derivatized to render them polycationic after synthesis; semiconductor nanocrystals can be rendered polycationic by addition of cationic species to their surface.

In a preferred embodiment, a conjugated polymer is used as the polycationic multichromophore.

Molecular structure of water-soluble, cationic, luminescent conjugated molecules.

Another example is shown in polymer 3 where the cationic water soluble conjugated polymer is poly((9,9-bis(6'-N,N,N-trimethylammonium)-hexyl)-fluorene phenylene) with iodide counteranions (denoted in the following as polymer 3).[36] The particular size of this polymer is not critical, so long as it is able to absorb light and transfer energy to signaling chromophores brought into proximity. Typical values of "n" fall within the range of two to about 100,000. This specific molecular structure is not critical; any water soluble cationic conjugated polymer with relatively high luminescence quantum efficiency can be used.

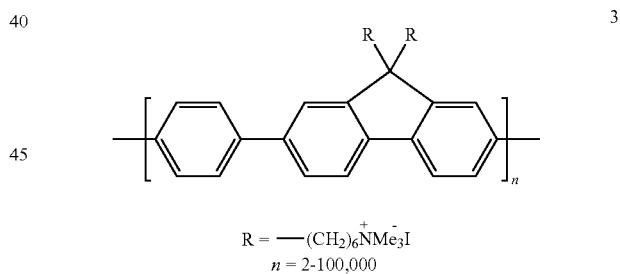

$R = -(CH_2)_6 \overset{+}{N}Me_3 I^-$
$n = 2\text{-}100,000$

Water soluble conjugated oligomers can also be used as the polycationic multichromophore. An example of such a water soluble, cationic, luminescent conjugated oligomer with iodide counterions is shown below (denoted herein as oligomer 4):

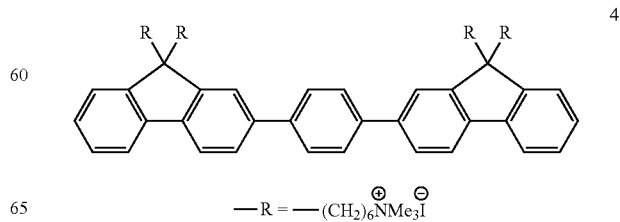

$-R = -(CH_2)_6 \overset{\oplus}{N}Me_3 \overset{\ominus}{I}$

Although the smaller oligomer 4 does not display the large signal amplification characteristic of a high molecular weight polymer, such smaller molecules are useful to deconvolute structure property relationships, which are difficult to determine with the inherent polydispersity and batch-to-batch variations found in polymers. Further, in aqueous media oligomers such as 4 are more soluble than their polymeric counterparts, and hydrophobic interactions are expected to be less important for 4 than for polymer structures. Assemblies of oligomers may thus be desired for specific applications.

The Sensor PBP

A sensor PBP is provided that binds to the target polynucleotide to be assayed. Chemical methods for attaching the signaling chromophore to the sensor PBP are known. Specific sensor PBP structures, including structures conjugated to chromophores, can be custom-made using commercial sources or chemically synthesized.

Any protein which can bind to a target polynucleotide of interest can be employed in the methods disclosed. Non-limiting examples of PBPs include DNA-binding proteins including transcription factors, splicing-factors, poly(A) binding proteins, chromatin components, viral proteins, proteins which detect viral infection, replication factors, and proteins involved in mitotic and/or meiotic cell division. RNA-protein interactions mediate important cellular processes including transcription, posttranscriptional modifications, RNA splicing, and translation[37,38,39,40]. The replication cycle of many pathogenic viruses, such as the human immunodeficiency virus type 1 (HIV-1)[41], picornaviruses[42] and influenza viruses[43], rely on specific RNA-protein interactions. The specificity of such interactions can be used as the basis for sequence specific sensors for utility in medical diagnostics and genomic studies. Exemplary polynucleotide binding proteins include zinc-finger proteins, homeodomain proteins, winged-helix (forkhead) proteins, leucine-zipper proteins, helix-loop-helix proteins, helix-turn-helix proteins, and histone-like proteins.

The PBPs may be isolated from a cell source, or may be produced in vitro, for example through in vitro transcription/translation methods or through completely synthetic methods. The PBPs can be naturally occurring proteins, mutants of naturally occurring proteins, randomly produced proteins produced, for example, by molecular evolution methods, or suspected polynucleotide binding proteins of unknown binding specificity.

One reason that monitoring RNA/protein interactions can be significant is that protein structures can serve as antibiotics that inhibit RNA function. One example is the interaction of the regulatory protein, Rev, with the Rev Responsive Element (RRE, a subdomain of the viral RNA) which is central to the human immunodeficiency virus (HIV) replication. Rev, which contains 116 amino acids, facilitates expression by inducing the accumulation of incompletely spliced viral mRNA transcripts in the cytoplasm. Protein/DNA binding and interactions are important because these events regulate various functions and metabolism of DNA. Proteins that exhibit this property are called sequence-specific DNA binding proteins. They mediate DNA replication, recombination, strand scission and transcription.

The Tat peptide used in the working examples is easily synthesized by the solid phase method and can be purified by HPLC and characterized by MALDI-TOF mass spectrum and amino acid analysis. The chemical methods for attaching the signaling chromophore to the peptide to form the signaling sensor PBP-C* are known.[44] A specific example is the signaling Tat-C* with fluorescein at the N-terminus. Specific PBP-C* structures can be made to order by commercial sources.

Other examples of PBP's which can be used include the matrix protein (M1, with a sequence of "DPNNMDKAVK-LYRKLKR" SEQ ID NO: 4; in single letter code) which binds to Type A influenza virus RNA, and hnRNP U protein ("MRGGNFRGGAPGNRGGYNRRGN" SEQ ID NO: 5; in single letter code) which binds to pre-ribosomal RNA. For example, M1 can be used in an assay to detect influenza virus in a sample, similar to the working example shown for HIV.

The Signaling Chromophore

Chromophores useful in the inventions described herein include any substance which can receive energy from an excited polycationic multichromophore in an appropriate solution and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, and green fluorescent protein.

Exemplary fluorescent dyes include fluorescein, 6-FAM, rhodamine, Texas Red®, tetramethylrhodamine, a carboxyrhodamine, carboxyrhodamine 6G, carboxyrhodol, carboxyrhodamine 110, Cascade Blue®dye, Cascade Yellow™ dye, coumarin, Cy2® dye, Cy3® dye, Cy3.5® dye, Cy5® dye, Cy5.5® dye, Cy-Chrome™ dye, phycoerythrin, PerCP™ dye (peridinin chlorophyll-a Protein), PerCP-CY™ 5.5dye, JOE (6-carboxy-4',5'-dichloro-2',7'dimethoxyfluorescein), NED™ dye, ROX™ dye (5-(and 6)-carboxy-X-rhodamine), HEX™ dye, Lucifer Yellow, Marina Blue™ dye, Oregon Green® 488 dye, Oregon Green® 500 dye, Oregon Green® 514 dye, Alexa Fluor® 350 dye, Alexa Fluor® 430 dye, Alexa Fluor® 488 dye, Alexa Fluor® 532 dye, Alexa Fluor® 546 dye, Alexa Fluor® 568 dye, Alexa Fluor® 594 dye, Alexa Fluor® 633 dye, Alexa Fluor® 647 dye, Alexa Fluor® 660 dye, Alexa Fluor® 680 dye, 7-amino-4-methylcoumarin-3-acetic acid, BODIPY® FL dye, BODIPY® FL-BR$_2$ dye, BODIPY® 530/555 dye, BODIPY® 558/568 dye, BODIPY® 564/570 dye, BODIPY® 576/589 dye, BODIPY® 581/591 dye, BODIPY® 630/650 dye, BODIPY® 650/665 dye, BODIPY® R6G dye, BODIPY® TMR dye, BODIPY® TR dye, conjugates thereof, and combinations thereof. Exemplary lanthanide chelates include europium chelates, terbium chelates and samarium chelates.

A wide variety of fluorescent semiconductor nanocrystals ("SCNCs") are known in the art; methods of producing and utilizing semiconductor nanocrystals are described in: PCT Publ. No. WO 99/26299 published May 27, 1999, inventors Bawendi et al.; U.S. Pat. No. 5,990,479 issued Nov. 23, 1999 to Weiss et al.; and Bruchez et al., Science 281:2013, 1998. Semiconductor nanocrystals can be obtained with very narrow emission bands with well-defined peak emission wavelengths, allowing for a large number of different SCNCs to be used as signaling chromophores in the same assay, optionally in combination with other non-SCNC types of signaling chromophores.

The term "green fluorescent protein" refers to both native *Aequorea* green fluorescent protein and mutated versions that have been identified as exhibiting altered fluorescence characteristics, including altered excitation and emission maxima, as well as excitation and emission spectra of different shapes (Delagrave, S. et al. (1995) Bio/Technology 13:151-154; Heim, R. et al. (1994) Proc. Natl. Acad. Sci. USA 91:12501-12504; Heim, R. et al. (1995) Nature 373: 663-664). Delgrave et-al. isolated mutants of cloned *Aequorea victoria* GFP that had red-shifted excitation spectra. Bio/

Technology 13:151-154 (1995). Heim, R. et al. reported a mutant (Tyr66 to His) having a blue fluorescence (Proc. Natl. Acad. Sci. (1994) USA 91:12501-12504).

The Substrate

For those variations of the assay performed on a substrate, the substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and includes semiconductor nanocrystals.

The substrate can take the form of a photodiode, an optoelectronic sensor such as an optoelectronic semiconductor chip or optoelectronic thin-film semiconductor, or a biochip. The location(s) of the individual sensor PBP(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using well known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface are chosen to provide appropriate optical characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

Assay components can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of arrays using mechanical synthesis strategies are described in, e.g., PCT Publication No. WO 93/09668 and U.S. Pat. No. 5,384,261.

Still further techniques include bead based techniques such as those described in PCT Appl. No. PCT/US93/04145 and pin based methods such as those described in U.S. Pat. No. 5,288,514.

Additional flow channel or spotting methods applicable to attachment of sensor PBPs to the substrate are described in U.S. patent application Ser. No. 07/980,523, filed Nov. 20, 1992, and U.S. Pat. No. 5,384,261. Reagents are delivered to the substrate by either (1) flowing within a channel defined on predefined regions or (2) "spotting" on predefined regions. A protective coating such as a hydrophilic or hydrophobic coating (depending upon the nature of the solvent) can be used over portions of the substrate to be protected, sometimes in combination with materials that facilitate wetting by the reactant solution in other regions. In this manner, the flowing solutions are further prevented from passing outside of their designated flow paths.

Typical dispensers include a micropipette optionally robotically controlled, an ink-jet printer, a series of tubes, a manifold, an array of pipettes, or the like so that various reagents can be delivered to the reaction regions sequentially or simultaneously.

Excitation and Detection of the Chromophores

Any instrument that provides a wavelength that can excite the polycationic multichromophore and is shorter than the emission wavelength(s) to be detected can be used for excitation. The excitation source preferably does not significantly excite the signaling chromophore directly. The source may be: a broadband UV light source such as a deuterium lamp with an appropriate filter, the output of a white light source such as a xenon lamp or a deuterium lamp after passing through a monochromator to extract out the desired wavelengths, a continuous wave (cw) gas laser, a solid state diode laser, or any of the pulsed lasers. The emitted light from the signaling chromophore can be detected through any suitable device or technique; many suitable approaches are known in the art. For example, a fluorimeter or spectrophotometer may be used to detect whether the test sample emits light of a wavelength characteristic of the signaling chromophore upon excitation of the multichromophore.

Kits

Kits comprising reagents useful for performing the methods of the invention are also provided. In one embodiment, a kit comprises a sensor PBP that binds to a target polynucleotide of interest and a polycationic multichromophore. The sensor PBP is conjugated to a signaling chromophore. In the presence of the target polynucleotide in the sample, the sensor PBP is brought into proximity to the multichromophore upon binding to the target, which associates electrostatically with the polycationic multichromophore.

The components of the kit are retained by a housing. Instructions for using the kit to perform a method of the invention are provided with the housing, and can be provided in any fixed medium. The instructions may be located inside the housing or outside the housing, and may be printed on the interior or exterior of any surface forming the housing which renders the instructions legible. The kit may be in multiplex form, containing pluralities of one or more different sensor PBPs which can bind to corresponding different target polynucleotides.

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available. The TAR RNA and dTAR RNA oligonucleotides described below were purchased from Dharmacon Research Inc. (Lafayette, USA). The polypeptides modified by fluorescein on the N-terminus (Tat-C* and SH3-C*) were custom-made by Sigma-Genosys (Texas, USA). The polymer 1 and oligomer 2 are prepared as described in the literature[45]. All the fluorescence and FRET experiments were carried out using a PTI Quantum Master fluorometer equipped with a Xenon lamp excitation source in tris-EDTA buffer solution (10 mM, pH=7.4).

Example 1

Figure 3:
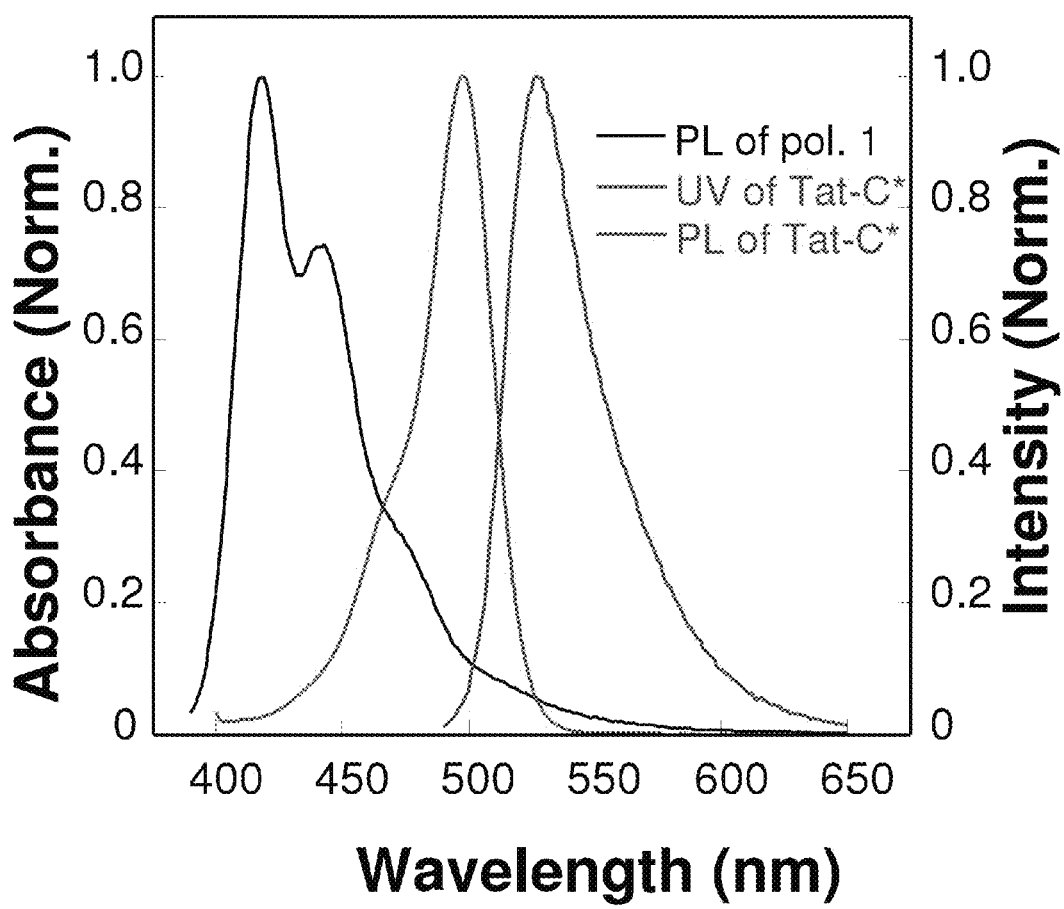
FIG. 3 shows the optical spectra of polymer 1 and Tat-C*. Excitations were done at 380 nm and 480 nm for polymer 1 and Tat-C*, respectively. Assay conditions are TRIS EDTA buffer solution (10 mM) and pH=7.4.

The emission spectra of the polymer 1, Tat-C* and the absorption spectra of Tat-C* are shown in FIG. 3. The data show that there is excellent overlap between the emission of polymer 1 and the absorption of Tat-C* to ensure fluorescence resonance energy transfer.

Example 2

Figure 4:
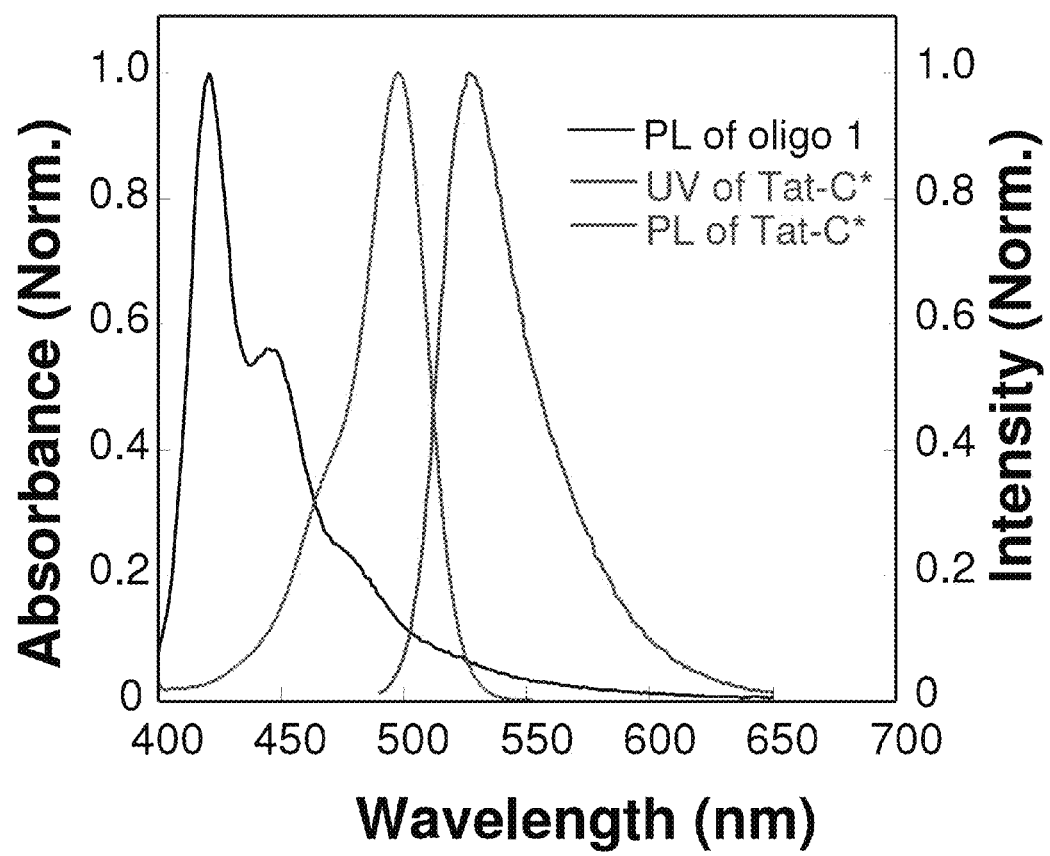
FIG. 4 shows the optical spectra of oligomer 1 and Tat-C*. Excitations were done at 365 nm and 480 nm for oligomer 1 and Tat-C*, respectively. Assay conditions are TRIS EDTA buffer solution (10 mM) and pH=7.4.

The emission spectra of the oligomer 1, Tat-C* and the absorption spectra of Tat-C* are shown in FIG. 4. The data show that there is excellent overlap between the emission of oligomer 1 and the absorption of Tat-C* to ensure fluorescence resonance energy transfer.

Example 3

Figure 5:
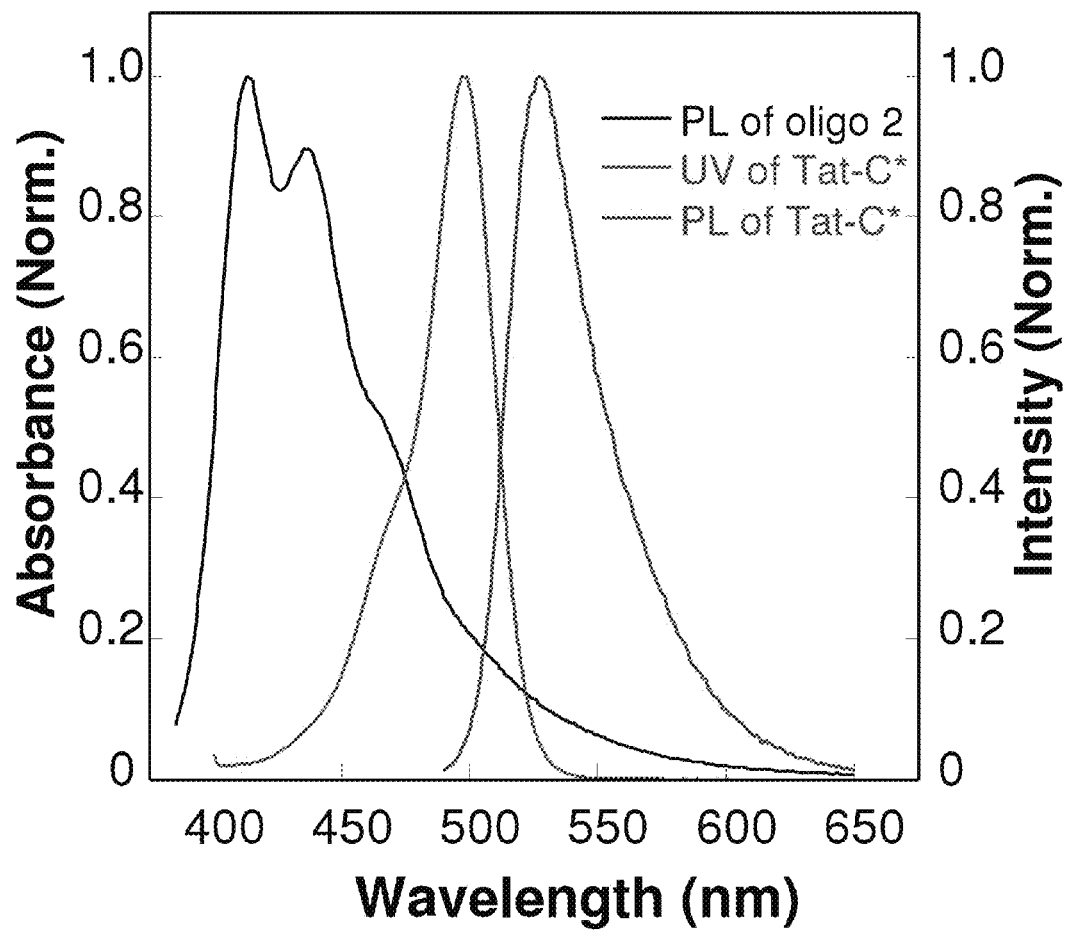
FIG. 5 shows the optical spectra of oligomer 2 and Tat-C*. Excitations were done at 375 nm and 480 nm for oligomer 2 and Tat-C*, respectively. Assay conditions are TRIS EDTA buffer solution (10 mM) and pH=7.4.

The emission spectra of the oligomer 2, Tat-C* and the absorption spectra of Tat-C* are shown in FIG. 5. The data show that there is excellent overlap between the emission of oligomer 2 and the absorption of Tat-C* to ensure fluorescence resonance energy transfer.

Example 4

The Tat-C* probe ([Tat-C*]=1.0×10-8 M) was mixed with an equimolar amount of the TAR RNA at room temperature, and in an identical fashion with a non-specific dTAR RNA. It is known that a bulge structure in TAR RNA is a requirement for Tat peptide binding to TAR RNA.[46,47] dTAR RNA is closely related in structure to TAR RNA, lacking the three base bulge structure necessary for Tat binding.

Figure 6:
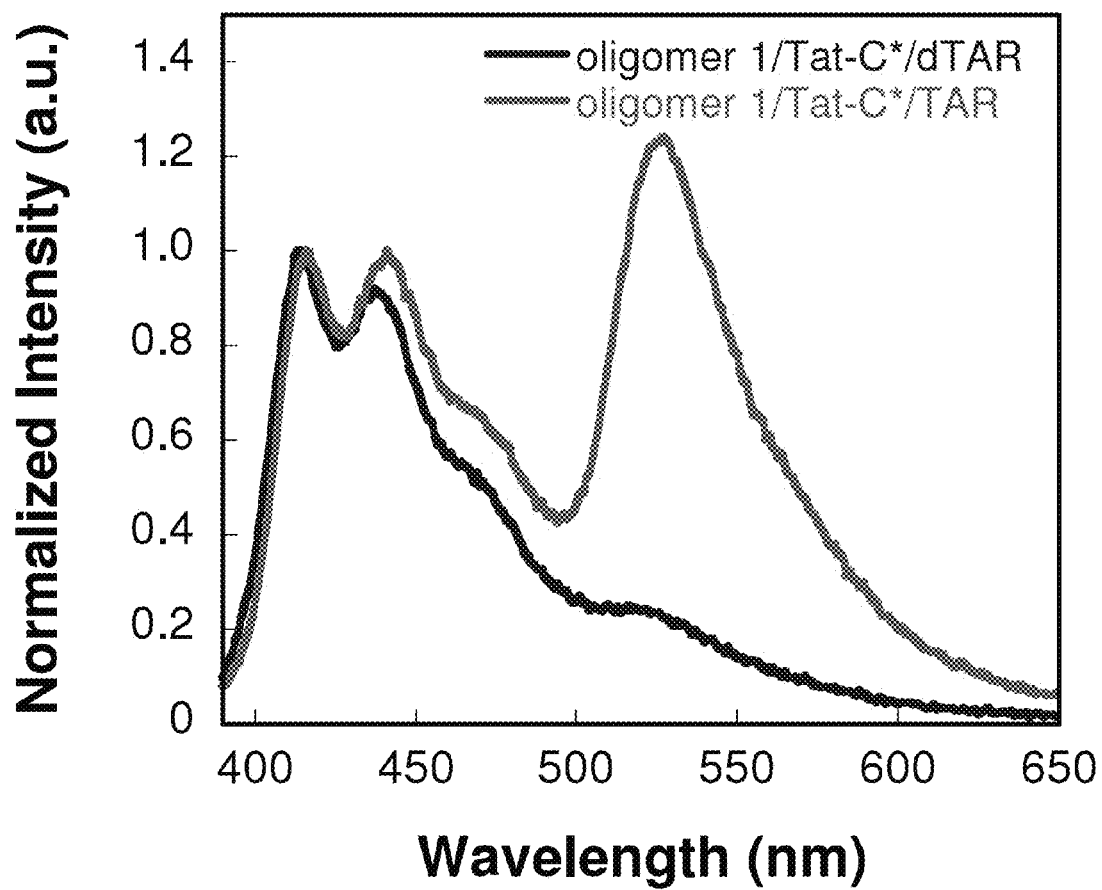
FIG. 6 shows the emission spectra of Tat-C* in the presence of TAR RNA and dTAR RNA by excitation of oligomer 1 at 365 nm. Conditions are in TRIS EDTA buffer solution (10 mM) and pH=7.4. The spectra are normalized with respect to the emission of oligomer 1.

Addition of oligomer 1 in water ([oligomer 1]=8.0×10-8 M) and subsequent comparison of the resulting fluorescence of Tat-C* obtained by excitation at 365 nm (FIG. 6) reveals an intensity ratio >10 times higher for the Tat-C*/TAR RNA, relative to the non-specific Tat-C*/dTAR RNA pair. These FRET differences demonstrate the specificity of the HIV TRA RNA sensor for a specific RNA. Furthermore, the fluorescein emission is more than 25 times larger than that obtained from direct Tat-C* excitation at the absorption maximum of fluorescein in the absence of oligomer 1. The increased Tat-C* emission in the energy transfer complex indicates that optical amplification is provided by the conjugated oligomer 1.

Example 5

Figure 7:
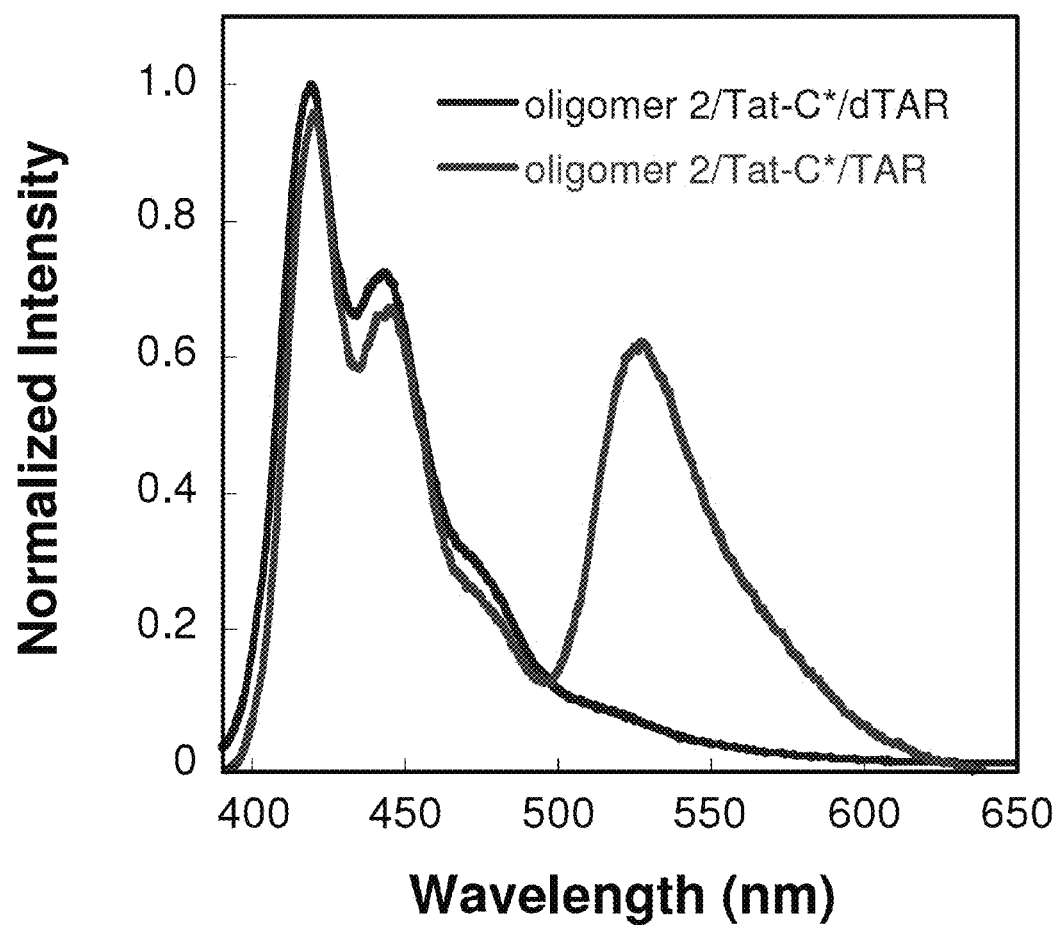
FIG. 7 shows the emission spectra of Tat-C* in the presence of TAR RNA and dTAR RNA by excitation of oligomer 2 at 375 nm. Conditions are in TRIS EDTA buffer solution (10 mM) and pH=7.4. The spectra are normalized with respect to the emission of oligomer 2.

The Tat-C* probe ([Tat-C*]=1.0×10$^{-8}$ M) was mixed with an equimolar amount of the TAR RNA at room temperature, and in an identical fashion with a non-specific dTAR RNA. Addition of oligomer 2 in water ([oligomer 2]=6.0×10$^{-8}$ M) and subsequent comparison of the resulting fluorescence of Tat-C* obtained by excitation at 375 nm (FIG. 7) reveals an intensity ratio 15 times higher for the Tat-C*/TAR RNA, relative to the non-specific Tat-C*/dTAR RNA pair. These FRET differences demonstrate the specificity of the HIV TRA RNA sensor of this invention to a specific RNA. Furthermore, the fluorescein emission is more than 30 times larger than that obtained from direct Tat-C* excitation in the absence of oligomer 2. The increased Tat-C* emission in the energy transfer complex indicates that optical amplification is provided by the conjugated oligomer 2.

Example 6

Figure 8:
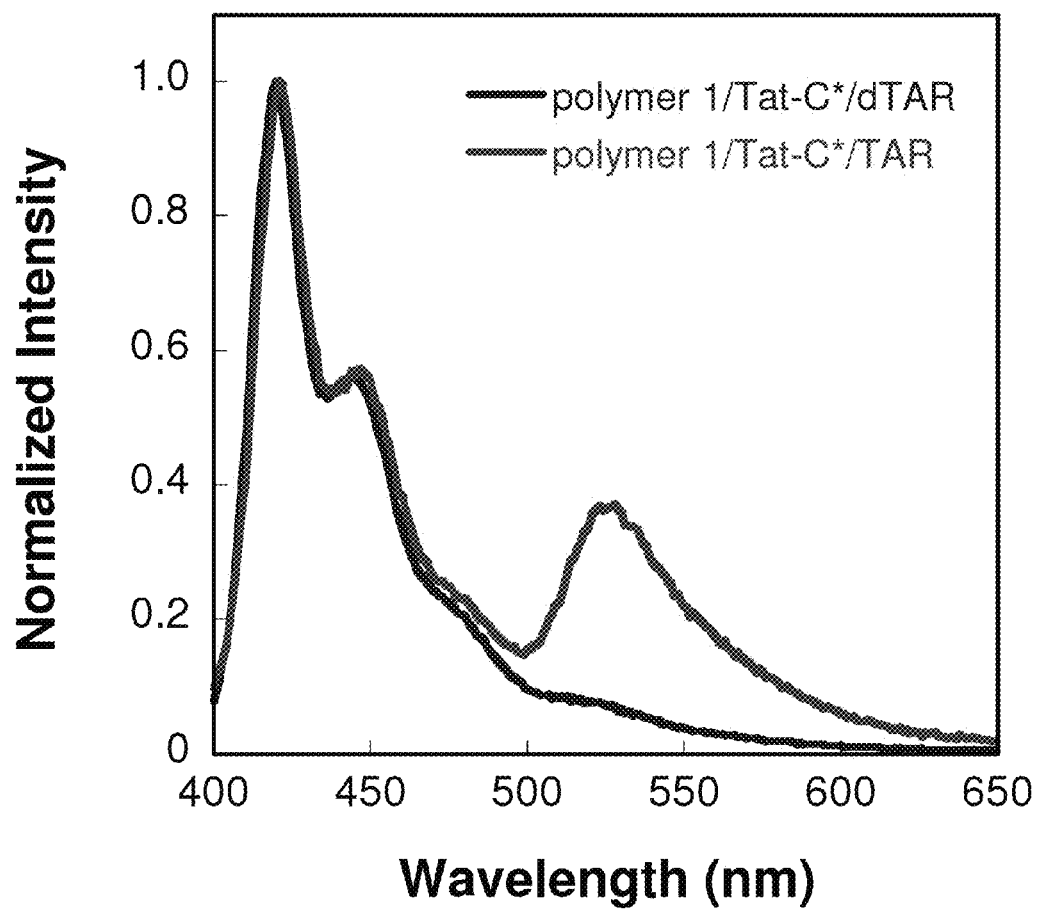
FIG. 8 shows the emission spectra of Tat-C* in the presence of TAR RNA and dTAR RNA by excitation of polymer 1 at 380 nm. Conditions are in TRIS EDTA buffer solution (10 mM) and pH=7.4. The spectra are normalized with respect to the emission of polymer 1.

The water soluble conjugated polymer 1 (average n=app. 15) was utilized as the light harvesting chromophore. The Tat-C* probe ([Tat-C*]=1.0×10$^{-8}$ M) was mixed with an equimolar amount of the TAR RNA at room temperature, and in an identical fashion with a non-specific dTAR RNA. Addition of polymer 1 in water ([polymer 1]=4.8×10$^{-7}$ M) into the mixture of Tat-C* and TAR RNA results in fluorescence of Tat-C* (FIG. 8) with an intensity ratio >15 times higher than that of the non-specific Tat-C*/dTAR RNA and 10 times larger than that obtained from direct Tat-C* excitation in the absence of polymer 1. Thus, significantly higher FRET ratios and correspondingly higher sensitivities can be achieved. Titration of 1 against the mixture of Tat-C* and TAR RNA revealed that the FRET ratio increased with the concentration of 1 until the ratio of charges from 1 to TAR RNA was close to 4:1, after which the FRET ratio was found to decrease. A similar pattern was observed for oligomer 2.

Example 7

Figure 9:
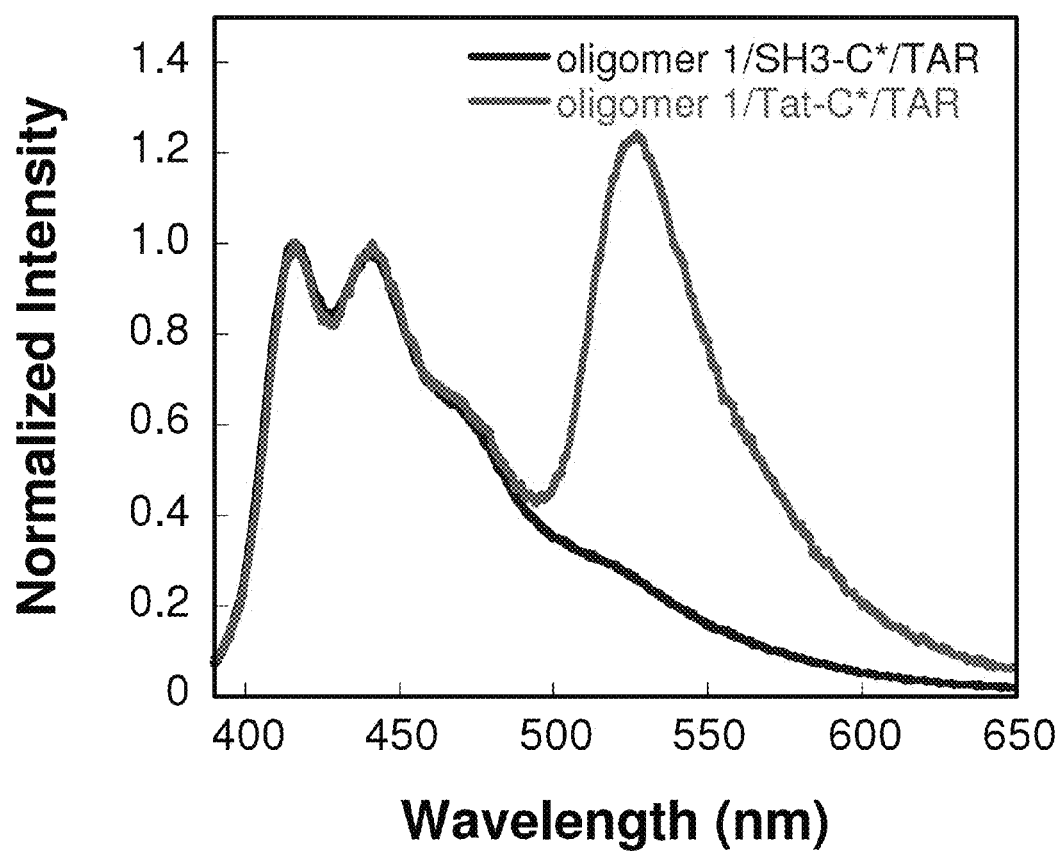
FIG. 9 shows the emission spectra of SH3-C* and Tat-C* in the presence of TAR RNA by excitation of oligomer 1 at 365 nm. Conditions are in TRIS EDTA buffer solution (10 mM) and pH=7.4. The spectra are normalized with respect to the emission of oligomer 1.

Another peptide sequence labeled with fluorescein at N-terminus (SH3-C*; AKPRPPRPLPVAC SEQ ID NO: 6; in single letter code) which cannot specifically binding to TAR RNA was also utilized as the signal probe. FIG. 9 ([SH3-C* or Tat-C*]=1.0×10$^{-8}$ M, [TAR RNA]=1.0×10$^{-8}$ M and [oligomer 1]=8.0×10$^{-8}$ M) shows C* emission only when the Tat-C* was present. These FRET differences demonstrate that the HIV TRA RNA sensor of this invention depends on the specific interaction of Tat peptide sequence with TAR RNA.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

REFERENCES

[1] Wang, J. *Nucleic Acid Res.* 2000 28 3011.
[2] Umek, R. M.; Lin, S. W.; Vielmetter, J.; Terbrueggen, R. H.; Irvine, B.; Yu, C. J.; Kayyem, J. F.; Yowanto, H.; Blackburn, G. F.; Farkas, D. H.; Chen, Y. P. *J. Mol. Diag.* 2001 3 74.
[3] Schork N. J.; Fallin D.; Lanchbury J. S. *Clini. Genet.* 2000 58 250.
[4] Balakin, K. V.; Korshun, V. A.; Mikhalev, I. I.; Maleev, G. V.; Malakhov A. D.; Prokhorenko, I. A.; Berlin, Yu. A. *Biosensors and Bioelectronics* 1998 13 771.
[5] LePecg, J. B.; Paoletti, C. *J. Mol. Biol.* 1967 27 87.
[6] Petty, J. T.; Bordelon, J. A.; Robertson, M. E. *J. Phys. Chem. B* 2000 104 7221.
[7] Cardullo, R. A.; Agrawal, S.; Flores, C.; Zamechnik, P. C.; Wolf, D. E. Proc. *Natl. Acad. Sci.* 1988 85 8790.
[8] Castro, A.; Williams, J. G. K. *Anal. Chem.* 1997-69 3915.
[9] Knemeyer, J.; Marmè, N.; Sauer, M. *Anal. Chem.* 2000 72 3717.
[10] N. J. Turro, *Modern Molecular Photochemistry*, University Science Books: Sausalito, Calif. 1991.
[11] J. R. Lakowicz, *Principles of fluorescence spectroscopy*, Kluwer Academic/Plenum Publishers, New York, 1999.
[12] R. Gallo, L. Montagnier, *Sci. Am.* 1988, 259 (10), 41.
[13] J. Wang, X. Cai, G. Rivas, H. Shiraishi, P. A. M. Farias, N. Dontha, *Anal. Chem.* 1996, 68, 2629.N. R. Isola, D. L. Stokes, T. Vo-Dinh, *Anal. Chem.* 1998, 70, 1352.
[14] J. Kuby, *Immunology*, W. Freeman Inc.: New York, 1991.
[15] D. S. Hage, *Anal. Chem.* 1999, 71, 294R.
[16] P. Nishanian, K. Huskins, S. Stehn, R. Detels, J. Fahey, *J. Infect. Dis.* 1990, 162, 21.
[17] J. Karn, M. J. Churcher, K. Rittner, A. Kelly, P. J. G. Butler, D. A. Mann, M. J. Gait, *HIV, a practical approach*, J. Karn, Ed., pp 147-165, IRL Press, New York, 1995.
[18] L. Chen, A. D. Frankel, *Proc. Natl. Acad. Sci. USA.* 1995, 92, 5077.
[19] A. D. Frankel, *Prot. Sci.* 1992, 1, 1539.
[20] C. Matsumoto, K. Hamasaki, H. Mihara, A. Ueno, *Bioorg. Med. Chem. Lett.* 2000, 10, 1857.
[21] I. C. Kwon, Y. H. Bae, S. W. Kim, *Nature,* 1991, 354,-291.
[22] D. Frankel, *Prot. Sci.* 1, 1539 (1992).
[23] K. M. Weeks, C. Ampe, S. C. Schultz, T. A. Steitz, D. M. Crothers, *Science* 249, 1281 (1 990).
[24] McQuade, D. T.; Pullen. A. E.; Swager, T. M. *Chem. Rev.* 2000 100 2537.
[25] Chen, L.; McBranch, D. W.; Wang, H.-L.; Helgeson, R.; Wudl, F.; Whitten, D. G. *Proc. Natl. Acad. Sci. U.S.A.* 1999 96 12287.
[26] Dogariu, A., Gupta, R., Heeger, A. J., Wang, H. *Synthetic Metals* 1999 100 95.
[27] Wang, J.; Wang, D.; Miller, E. K.; Moses, D.; Bazan, G. C.; Heeger, A. J. *Macromolecules* 2000 33 5153.
[28] Stork, M. S.; Gaylord, B. S.; Heeger, A. J.; Bazan, G. C. *Adv. Mater.* 2002 14 361. The molecular weight of polymer 1 was determined to be 8,600 g/mole ($M_n$).
[29] Kabanov, A. V.; Felgner, P.; Seymour, L. W., Eds. *Self-Assembling Complexes for Gene Delivery. From Laboratory to Clinical Trial*; John Wiley: Chichester, 1998.
[30] Kircheis, R.; Blessing, T.; Brunner, S.; Wightman, L.; Wagner, E. *J. Controlled Release* 2001 72 165.
[31] Wolfert, M. A.; Dash, P. R.; Navarova, O.; Oupicky, D.; Seymour, L. W.; Smart, S.; Strohalm, J.; Ulbrich, K. *Bioconjugate Chem.* 1999 10 993.
[32] Ganachaud, F.; Elaïssari, A.; Pichot, C.; Laayoun, A.; Cros, P. *Langmuir* 1997 13 701.
[33] Smith, J. O.; Olson, D. A.; Armitage, B. A. *J. Am. Chem, Soc.* 1999 121 2628.
[34] Harada, A.; Kataoka, K. *Science* 1999 283 65.
[35] Bronich, T. K.; Nguyen, H. K.; Eisenberg, A.; Kabanov, A. V. *J. Am. Chem. Soc.* 2000 122 8339.
[36] Stork, M. S.; Gaylord, B. S.; Heeger, A. J.; Bazan, G. C. *Adv. Mater.* 2002 14 361.
[37] K. Nagai, I. W. Mattay, RNA-Protein Interactions. Frontiers in Molecular Biology Series (Oxford University Press, Oxford, UK, 1994).
[38] G. Varani, *Acc. Chem. Res.* 30, 189 (1997).
[39] Y. N. Vaishnav, F. Wong-Staal, *Ann. Rev. Biochem.* 60, 577 (1991).
[40] C. Jain. J. G. Belasco, *Methods Enzymol.* 318, 309 (2000).
[41] B. A. Sullenger, E. Gilboa, *Nature* 418, 252 (2002).
[42] E. V. Pilipenko et al., *Genes Dev.* 14, 2028 (2000).
[43] Portela, P. Digard, *J. Gen. Virol.* 83, 723 (2001).
[44] G. T. Hermanson, *Bioconjugate Techniques*, Academic Press, San Diego, 1996.
[45] J. Futami et al., *J. Biochem.* 132, 223 (2002).
[46] S. Richter, H. Cao, T. M. Rana, *Biochemistry* 41, 6391 (2002).
[47] J. D. Puglisi, R. Tan, B. J. Calnan, A. D. Frankel, J. R. Williamson, *Science* 257, 76 (1992).

What is claimed is:

1. A method of assaying a sample for the presence of a target polynucleotide that binds to a polynucleotide binding protein selected from the group consisting of Tat, matrix protein M1, and hnRNP U, the method comprising:

(a) contacting the sample with:

(i) a sensor polynucleotide binding protein (sensor PBP) that comprises a polynucleotide binding protein selected from the group consisting of Tat, matrix protein M1, and hnRNP U linked to a signaling chromophore, wherein the signaling chromophore comprises a fluorophore; and (ii) a conjugated polymer that interacts with the target polynucleotide and upon excitation transfers energy to the signaling chromophore when the sensor PBP, target polynucleotide and conjugated polymer are present in a complex, wherein the conjugated polymer has the structure

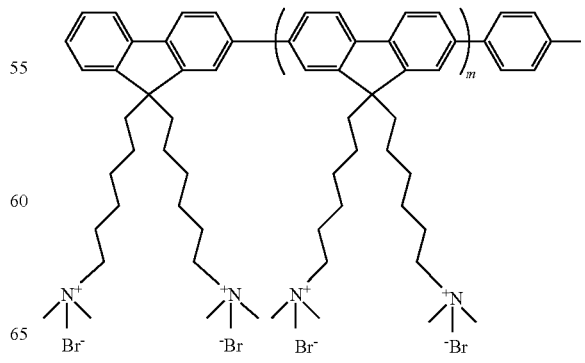

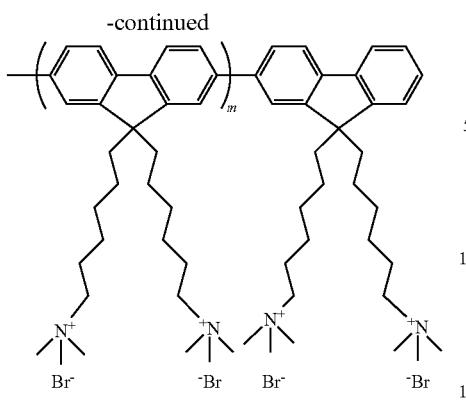

wherein m=1 or 2;

(b) applying a light source to the sample that excites the conjugated polymer of the complex if present;

(c) detecting light emitted from the signaling chromophore if emitted; and

10. The method according to claim 1, wherein the polynucleotide binding protein is matrix protein M1 and the target polynucleotide is Type A influenza virus RNA.

11. The method according to claim 1, wherein the polynucleotide binding protein is hnRNP U and the target polynucleotide is pre-ribosomal RNA.

12. A method of assaying a sample for the presence of a target polynucleotide that binds to a polynucleotide binding protein selected from the group consisting of Tat, matrix protein M1, and hnRNP U, the method comprising:
(a) contacting the sample with:
(i) a sensor polynucleotide binding protein (sensor PBP) that comprises a polynucleotide binding protein selected from the group consisting of Tat, matrix protein M1, and hnRNP U linked to a signaling chromophore, wherein the signaling chromophore comprises a fluorophore; and
(ii) a conjugated polymer that interacts with the target polynucleotide and upon excitation transfers energy to the signaling chromophore when the sensor PBP, target polynucleotide and conjugated polymer are present in a complex, wherein the conjugated polymer has the structure

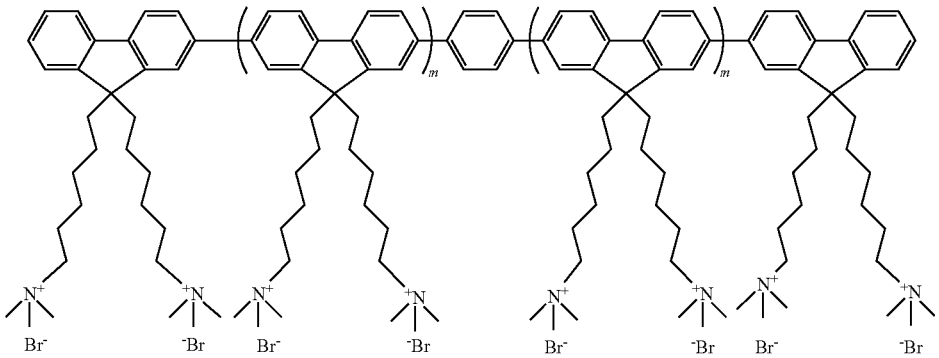

(d) evaluating whether the light emitted from the signaling chromophore is above a threshold level that indicates that the target polynucleotide is present in the sample.

2. The method according to claim 1, wherein the sample is contacted with a plurality of different sensor PBPs, said different sensor PBPs comprising a corresponding different signaling chromophore, wherein each of said different sensor PBPs binds to a corresponding different target polynucleotide.

3. The method according to claim 1, wherein the fluorophore is selected from the group consisting of a semiconductor nanocrystal, a fluorescent dye, a lanthanide chelate and a green fluorescent protein.

4. The method according to claim 3, wherein the fluorophore is a semiconductor nanocrystal.

5. The method according to claim 3, wherein the fluorophore is a fluorescent dye.

6. The method according to claim 5, wherein the fluorescent dye is fluorescein.

7. The method according to claim 5, wherein the fluorophore is a lanthanide chelate.

8. The method according to claim 1, wherein the method comprises determining the relative amount of light emitted from the signaling chromophore as compared to a control.

9. The method according to claim 1, wherein the polynucleotide binding protein is Tat and the target polynucleotide is TAR RNA.

wherein m=1 or 2;

(b) applying a light source to the sample that excites the conjugated polymer of the complex if present;

(c) detecting light emitted from the signaling chromophore if emitted, wherein the emission is at least 10 times larger than that obtained from direct excitation of the signaling chromophore; and (d) evaluating whether the light emitted from the signaling chromophore is above a threshold level that indicates that the target polynucleotide is present in the sample.

13. The method according to claim 12, wherein the emission is at least 25 times larger than that obtained from direct excitation of the signaling chromophore.

14. The method according to claim 12, wherein the emission is at least 30 times larger than that obtained from direct excitation of the signaling chromophore.

15. The method according to claim 12, wherein the polynucleotide binding protein is Tat and the target polynucleotide is TAR RNA.

16. The method according to claim 12, wherein the polynucleotide binding protein is matrix protein M1 and the target polynucleotide is Type A influenza virus RNA.

17. The method according to claim 12, wherein the polynucleotide binding protein is hnRNP U and the target polynucleotide is pre-ribosomal RNA.

* * * * *